US 6,694,975 B2

(12) United States Patent
Schuster et al.

(10) Patent No.: US 6,694,975 B2
(45) Date of Patent: Feb. 24, 2004

(54) TEMPERATURE CONTROLLING DEVICE FOR AEROSOL DRUG DELIVERY

(75) Inventors: Jeffrey A. Schuster, Oakland, CA (US); Joan Rosell, Castro Valley, CA (US); Avi Eliahu, Oakland, CA (US); Christopher J. Flaim, Modesto, CA (US)

(73) Assignee: Aradigm Corporation, Hayward, CA (US)

( * ) Notice: Subject to any disclaimer, the term of this patent is extended or adjusted under 35 U.S.C. 154(b) by 86 days.

(21) Appl. No.: 09/960,642

(22) Filed: Sep. 20, 2001

(65) Prior Publication Data

US 2002/0112723 A1 Aug. 22, 2002

Related U.S. Application Data

(63) Continuation-in-part of application No. 09/690,242, filed on Oct. 16, 2000, now Pat. No. 6,263,872, which is a continuation of application No. 09/107,306, filed on Jun. 30, 1998, now Pat. No. 6,131,570, which is a continuation-in-part of application No. 08/752,946, filed on Nov. 21, 1996, now Pat. No. 5,906,202.

(51) Int. Cl.[7] .............................................. A61M 16/00
(52) U.S. Cl. ........................... 128/203.26; 128/203.27; 128/204.17; 219/538; 338/280
(58) Field of Search ................................. 338/280, 283; 392/343, 383, 384; 219/530, 538; 128/203.17, 203.26, 203.27, 204.17

(56) References Cited

U.S. PATENT DOCUMENTS

| 608,928 | A | * | 8/1898 | Taylor | 392/383 |
|---|---|---|---|---|---|
| 815,915 | A | * | 3/1906 | Fallek | 392/383 |
| 897,326 | A | * | 9/1908 | Wade | 338/58 |
| 905,045 | A | * | 11/1908 | Ayer et al. | 338/253 |
| 938,671 | A | * | 11/1909 | Leonard | 338/58 |
| 1,535,901 | A | * | 4/1925 | Clark | 392/422 |
| 1,614,330 | A | * | 1/1927 | Wiegard | 338/240 |
| 1,694,351 | A | * | 12/1928 | Long | 392/383 |
| 1,721,911 | A | * | 7/1929 | Kemble | 338/58 |
| 1,967,757 | A | * | 7/1934 | Losee | 392/365 |
| 1,976,651 | A | * | 10/1934 | Brantingham | 392/365 |
| 1,976,652 | A | * | 10/1934 | Brantingham | 392/365 |
| 1,997,776 | A | * | 4/1935 | Hogel | 392/485 |

(List continued on next page.)

OTHER PUBLICATIONS

Bates, David V., et al., (1966) "Deposition and Retention Models for Internal Dosimetry of the Human Respiratory Tract", *Health Physics*, vol. 12:173–207.

Byron, Peter R., (1986) "Prediction of Drug Residence Times in Regions of the Human Respiratory Tract Following Aerosol Inhalation", *J. of Pharm. Sciences*, vol. 75(5):433–438.

Farr, Stephen J., et al., (1996) "AERx–Development of a Novel Liquid Aerosol Delivery System Concept to Clinic", *Respiratory Drug Delivery V*, pp. 175–185.

Ferron et al. (1988) "Inhalation of Salt Aerosol Particles—II. Growth and Deposition in the Human Respiratory Tract." *J. Aerosol Sci.*, vol. 19(5):611–631.

(List continued on next page.)

*Primary Examiner*—Aaron J. Lewis
(74) *Attorney, Agent, or Firm*—Carol M. LaSalle; Bozicevic, Field & Francis LLP

(57) ABSTRACT

A portable air temperature controlling device useful for warming air surrounding an aerosolized drug formulation. Warming the air of an aerosol makes it possible to reduce the diameter of aerosol particles produced by an aerosol generation device. Additionally, warming the air forces the diameter of the aerosol particles to be in the range required for systemic drug delivery independent of ambient conditions. Smaller particles can be more precisely targeted to different areas of the respiratory tract.

27 Claims, 7 Drawing Sheets

U.S. PATENT DOCUMENTS

| | | | | |
|---|---|---|---|---|
| 2,071,186 A | * | 2/1937 | Tofano | 604/291 |
| 2,153,239 A | * | 4/1939 | Curci | 392/383 |
| 2,192,732 A | * | 3/1940 | Johnson | 219/261 |
| 2,498,157 A | * | 2/1950 | Farr | 392/368 |
| 2,761,055 A | * | 8/1956 | Ike | 392/393 |
| 3,214,572 A | * | 10/1965 | Young | 219/550 |
| 3,219,797 A | * | 11/1965 | Brady | 392/384 |
| 3,265,865 A | * | 8/1966 | Hager, Jr. | 219/549 |
| 3,346,720 A | * | 10/1967 | Siegla | 219/461.1 |
| 3,651,304 A | * | 3/1972 | Fedor | 219/200 |
| 3,775,590 A | * | 11/1973 | Gartner | 392/367 |
| 3,797,475 A | * | 3/1974 | Hughes | 126/206 |
| 3,835,435 A | * | 9/1974 | Seel | 338/280 |
| 3,933,276 A | | 1/1976 | Packham et al. | |
| 4,097,719 A | * | 6/1978 | Olsen et al. | 392/345 |
| 4,142,062 A | * | 2/1979 | Wentworth | 373/134 |
| 4,563,572 A | * | 1/1986 | Hager, Jr. | 392/423 |
| 4,587,966 A | | 5/1986 | Albarda | |
| 4,620,086 A | * | 10/1986 | Ades et al. | 219/552 |
| 4,653,494 A | | 3/1987 | Ruderian | |
| 4,853,517 A | * | 8/1989 | Bowen et al. | 392/390 |
| 4,922,901 A | | 5/1990 | Brooks et al. | |
| 4,947,875 A | | 8/1990 | Brooks et al. | |
| 5,038,769 A | | 8/1991 | Krauser | |
| 5,497,763 A | | 3/1996 | Lloyd et al. | |
| 5,507,103 A | * | 4/1996 | Merritt | 34/97 |
| 5,522,385 A | | 6/1996 | Lloyd et al. | |
| 5,641,421 A | * | 6/1997 | Manov et al. | 219/553 |
| 5,651,906 A | * | 7/1997 | Whittenberger et al. | 219/552 |
| 5,660,166 A | | 8/1997 | Lloyd et al. | |
| 5,665,262 A | | 9/1997 | Hajaligol et al. | |
| 5,672,581 A | | 9/1997 | Rubsamen et al. | |
| 5,709,202 A | | 1/1998 | Lloyd et al. | |
| 5,718,222 A | | 2/1998 | Lloyd et al. | |
| 5,906,202 A | * | 5/1999 | Schuster et al. | 128/203.23 |
| 6,072,938 A | * | 6/2000 | Peterson et al. | 392/343 |
| 6,131,570 A | * | 10/2000 | Schuster et al. | 128/203.26 |
| 6,222,987 B1 | * | 4/2001 | Duke et al. | 392/383 |
| 6,263,872 B1 | * | 7/2001 | Schuster et al. | 128/203.26 |
| 6,441,347 B1 | * | 8/2002 | Wu | 219/438 |

OTHER PUBLICATIONS

Hickey, A.J., et al., (1990) "Effect of Hydrophobic Coating on the Behavior of a Hygroscopic Aerosol Powder in an Environment of Controlled Temperature and Relative Humidity", *J. of Pharm. Sciences*, vol. 79(11):1009–1014.

Morrow et al. (1966) "Deposition and retention models for internal dosimetry of the human respiratory tract. Task group on lung dynamics." *Health Phys.*, vol. 12(2):173–207.

Phipps, Paul R., et al., (1990) "Droplets Produced by Medical Nebulizers: Some Factors Affecting Their Size and Solute Concentration" *Chest*, vol. 97:1327–1332.

Stahlhofen et al. (1980) "Experimental determination of the regional deposition of aerosol particles in the human respiratory tract." *Am Ind Hyg Assoc J.*, vol. 41(6):385–98a.

* cited by examiner

TEMPERATURE CONTROLLING DEVICE FOR AEROSOL DRUG DELIVERY

CROSS-REFERENCES

This application is a continuation-in-part application of U.S. Ser. No. 09/690,242 filed Oct. 16, 2000 (issued Jul. 24, 2001 as U.S. Pat. No. 6,263,872) which is a continuation of U.S. application Ser. No. 09/107,306 filed Jun. 30, 1998 (issued Oct. 17, 2000 as U.S. Pat. No. 6,131,570) which is a continuation-in-part of U.S. application Ser. No. 08/752,946 filed Nov. 21, 1996, now issued U.S. Pat. No. 5,906,202 which applications and patents are incorporated herein by reference and to which applications we claim priority under 35 U.S.C. '120.

FIELD OF THE INVENTION

This invention relates generally to portable devices and methods useful for optimizing the diameter distribution of a medical aerosol, and reducing the amount of variability arising from variations in ambient conditions. More specifically, this invention relates to portable devices for controlling the temperature of air to be mixed with aerosol particles of drugs to be delivered to the lung.

BACKGROUND OF THE INVENTION

There are several known methods for the aerosolized delivery of drugs. In general, the methods include: (1) placing an aqueous formulation within a nebulizer device which by various mechanical means causes the drug formulation to be aerosolized in a continuous stream which is inhaled by the patient; (2) dry powder inhalers which create a fine powder of the drug and aerosolize the powder in a dust form which is inhaled; (3) metered dose inhalers which dissolve or disperse the drug in a low boiling point propellant; and (4) more current devices such as that disclosed within U.S. Pat. No. 5,660,166 issued Aug. 26, 1997 which force aqueous formulations through a nozzle to create an aerosol which is inhaled by the patient.

In accordance with each of the known methods for aerosolizing a drug it is important to produce an aerosol which has particles within a desired diameter range, e.g. 0.5 to 12.0 microns and more preferably 1.0 to 3.5 microns. In addition to producing small particles it is preferable to produce particles which are relatively consistent in diameter, i.e. produce an aerosol wherein a large percentage of the particles fall within the desired diameter range. In addition, it is desirable to produce an aerosol which has the property that the key measures of aerosol quality, such as particle diameter and dose emitted are not effected by ambient conditions such as temperature and or relative humidity. With any of the known methods for aerosol delivery of drugs there are difficulties with respect to making the particles sufficiently small. Along with these difficulties there are difficulties with respect to creating particles which are relatively consistent in diameter. These difficulties are particularly acute when attempting to provide for systemic delivery of an aerosolized drug. Efficient systemic delivery requires that the aerosol be delivered deeply into the lung so that the drug can efficiently reach the air/blood exchange membranes in the lung and migrate into the circulatory system.

Aerosol delivery to the lungs has been used for delivery of medication for local therapy (Graeser and Rowe, *Journal of Allergy* 6:415 1935). The large surface area, thin epithelial layer, and highly vascularized nature of the peripheral lung (Taylor, *Adv. Drug Deliv. Rev.* 5:37 1990) also make it an attractive site for non-invasive systemic delivery. Unlike other avenues of non-invasive delivery such as trans-dermal, nasal, or buccal, the lung is designed as a portal of entry to the systemic circulation. However, targeting the peripheral lung requires careful control of the aerosol particle diameter and velocity distributions, in order to by pass the exquisitely evolved particle filtering and clearing functions of the bronchial airways.

Many authors have reported results of experiments or mathematical models showing that micron sized particles are required for delivery to the lungs (c.f. Stahlhofen, Gebhart and Heyder, *Am. Ind. Hyg. Assoc. J.* 41:385 1980, or Ferron, Kreyling and Haider, *J. Aerosol Sci.* 19:611 1987). One example is the model of the Task Group on Lung Dynamics (Morrow et. al. *Health Physics* 12:173 1966). As FIG. 1 shows, under the assumptions of this model, particles of diameter less than ~3.5 $\mu$m are required to avoid the oropharynx and bronchial airways. FIG. 1 might suggest that the maximum efficiency of deposition of drugs delivered to the pulmonary region of the lung is limited to ~60%. However, as can be seen in FIG. 2, efficiencies approaching 100% can be achieved by allowing the particles to settle gravitationally during a ten second breath hold (Byron, *J. Pharm. Sci.* 75:433 1986).

It has been demonstrated that ambient conditions can strongly effect the amount of aerosol particles less than 3.5 $\mu$m emitted from aerosol generation device. One example is the work of Phipps and Gonda (*Chest* 97:1327–1332, 1990) showing that the amount of aerosol less than 3.5 $\mu$m delivered by an aerosol drug delivery device changed from 33% to 73% when the relative humidity changed from 100% to 70%. Similar work with a dry powder (Hickey et al *J. Pharm. Sci.* 79, 1009–1011) demonstrated a change in the amount of aerosol less than 3.5 $\mu$m from 9% to 42% when the ambient relative humidity changed from 97% to 20%. These data are tabulated in Table 1.

TABLE 1

Effect of RH on Particle Diameter Distribution

| Aerosol | T, °C. | R. H., % | % <3.5 $\mu$m |
| --- | --- | --- | --- |
| Isotonic Saline[1], Hudson Up-Draft | 23–24° | 100% | 33% |
| Isotonic Saline[1], Hudson Up-Draft | 23–24° | 65–75% | 73% |
| Fluorescein Powder[2] | 37 ± 0.1° | 97 ± 1% | 9% |
| Fluorescein Powder[2] | 37 ± 0.1° | 20 ± 5% | 42% |

[1]Phipps and Gonda, 1990
[2]Hickey et al 1990

A device useful for controlling the temperature of the air surrounding an aerosolized drug formulation is provided in U.S. Pat. No. 6,131,570, which issued on Oct. 17, 2000. An element is preheated prior to aerosolizing the drug formulation. After preheating has been accomplished, the drug formulation is aerosolized substantially contemporaneously with the control of air flow through a space in which the preheated element is contained, whereby heated air mixes with the aerosolized drug formulation, thereby evaporating liquid carrier from the aerosol particles to obtain smaller particles to be delivered to the lungs of the patient.

Since devices of this type are designed to be portable, primary goals include making the heating element as efficient as possible for performing the functions of rapidly heating up and storing energy during the preheat stage, as well as rapidly releasing heat to the air as it flows by the heating element to be delivered to the aerosolized drug.

Efficient storing and releasing of heat energy are basically contradictory in nature, however, and these goals remain a problem to be addressed, since increasing the efficiency of these features allows a reduction in the size and weight of the power source which must necessarily be included in a portable device.

Many pharmaceutical compounds of a wide range of molecular weights are potential candidates for systemic delivery via the lung. Small molecules analgesics such as morphine or fentanyl could be delivered to pain patients, e.g. cancer or post-operative patients. Morphine has demonstrated bioavailability when delivered via the lung (S. J. Farr, J. A. Schuster, P. M. Lloyd, L. J. Lloyd, J. K. Okikawa, and R. M. Rubsamen. In R. N. Dalby, P. R. Byron, and S. J. Farr (eds.), *Respiratory Drug Delivery V*, Interpharm Press, Inc., Buffalo Grove, 1996, 175–185).

Potent peptide hormones are available for a variety of therapeutic indications. Leuprolide, for example, is a GnRH super-agonist useful in the treatment of endometriosis and prostate cancer. Leuprolide also has potential applications in the field of breast cancer management and the treatment of precocious puberty. Calcitonin enhances metabolism and may be a useful therapeutic agent for the management of osteoporosis, a common complication of aging.

To treat conditions or diseases of the endocrine system, pharmaceutical formulations containing potent peptide hormones are typically administered by injection. Because the stomach presents a highly acidic environment, oral preparations of peptides are unstable and readily hydrolyzed in the gastric environment. Currently, there are no oral preparations of therapeutic peptide agents commercially available.

Both calcitonin and leuprolide can be administered nasally. (See Rizzato et al., *Curr. Ther. Res.* 45:761–766, 1989.) Both drugs achieve blood levels when introduced into the nose from an aerosol spray device. However, experiments by Adjei et al. have shown that the bioavailability of leuprolide when administered intranasally is relatively low. However, an increase in the bioavailability of leuprolide can be obtained by administering the drug into the lung. Intrapulmonary administration of leuprolide has been shown to be an effective means of non-invasive administration of this drug (Adjei and Garren, *Pharmaceutical Research*, Vol. 7, No. 6, 1990).

Intrapulmonary administration of drugs has the advantage of utilizing the large surface area available for drug absorption presented by lung tissue. This large surface area means that a relatively small amount of drug comes into contact with each square centimeter of lung parenchyma. This fact reduces the potential for tissue irritation by the drug and drug formulation. Local irritation has been seen with nasal delivery of insulin and has been a problem for commercialization of nasal preparations of that drug. It is a problem with peptide hormones that they are very potent with effects that are not immediately manifested. For example, therapy with leuprolide for prostate cancer does not typically produce any acute clinical effects. Similarly, prophylaxis against osteoporosis with calcitonin will not produce any acute symptoms discernible to the patient. Therefore, administration of each dose of these drugs must be reliable and reproducible.

SUMMARY OF THE INVENTION

A portable, self-contained device useful for controlling the temperature of the air surrounding an aerosolized drug formulation is provided, as well as methods for more efficiently transferring heat energy to air which is thereby warmed and applied to the drug formulation. A method of dissipating power to store heat, and then releasing the stored heat to warm a bolus of air, and a device for carrying out such method are provided. Such a method includes supplying power from a portable power source to a heating element; storing heat in the heating element as power is supplied from the portable power source; determining when the heating element achieves a predetermined operating temperature; and flowing air over the heating element after the heating element has achieved the predetermined operating temperature, to release heat to the flowing air, whereby the thermal time constant of the device may be greater than about 10 seconds in still air, preferably greater than about 15 seconds, more preferably greater than about 20 seconds, still more preferably greater than about 30 seconds and most preferably greater than about 40 seconds, and the thermal constant of the device for releasing heat to the flowing air is less than about 15 seconds, more preferably less than about 7 seconds, even more preferably less than about 5 seconds.

During the preheat phase, as heat is stored in the heating element, it is noted that energy may be distributed within the heating element. For example, a primary element may be heated, and some or all of the heat generated may be distributed to a secondary element for storage.

The flowing air may be driven by inhalation by a user on a channel fluidly connected with the heating element. However, it would also be possible to construct a heating device employing some other driver for passing air over the heating element (such as an electric fan, for example) to warm the air in much the same manner that the inhaled air is warmed. The patient could subsequently inhale the evaporated drug from a holding chamber into which the fan blows the warmed air (which evaporates the drug and carries it to the holding chamber). The portable power source may comprise at least one battery cell with or without at least one capacitor, for example.

The present invention includes modifications of a heating device, and particularly heating element to increase the thermal time constant of the heating device in still air. Such modifications may include coating the thermal element with gold; providing a shield around the heating element and, optionally, one or more shield closing elements, to reflect radiant heat, mitigate losses from the heating element to the channel due to free convection, and to absorb some heat that would otherwise have been lost from the heating element during storing of heat, wherein the shield (and optionally, shield closing elements) function(s) as a secondary heat storage element that can subsequently release heat for warming the moving air; coating the shield and or shield closing elements with gold; and combinations thereof.

Modifications of a heating device to optimize the thermal time constant of the heating device in moving air are also disclosed. Such characteristics may include configuring one or more passive elements to absorb heat from and release heat to the moving air. The heating element may comprise a shape that enhances heat transfer in moving air.

Hand-held, portable air temperature controlling devices are disclosed which comprise a heating element adapted to receive energy from a self-contained, portable power source and store the energy as heat during a preheat operation; and a housing surrounding the heating element and defining an air flow path through which air flows over the heating element to transfer heat to the air during an air warming operation; wherein a thermal time constant of the heating device in still air during the preheat operation is greater than about 15 seconds and a thermal time constant of the heating device in moving air during the warming operation is less than about 15 seconds.

A shield may be provided to substantially surround the heating element, while remaining open at opposite ends to allow air to pass therethrough. Optionally, a shield closing element may be provided in one or each open end to further shield and surround the heating element during preheat, while allowing air flow therethrough during an air warming operation.

A passive element may be provided downstream of the heating element, wherein the passive element conditions a heat pulse generated when air flows over the heating element to transfer heat to the air during the air warming operation.

An air temperature controlling device is further disclosed as comprising a self-contained, portable power source adapted to connect with the heating (or thermal) element to supply power thereto.

In one example, a hand-held, portable air temperature controlling device comprises a heating element adapted to receive energy from a self-contained, portable power source and store the energy as heat during a preheat operation; and a housing surrounding the heating element and defining an air flow path through which air flows over the heating element to transfer heat to the air during an air warming operation; wherein the heating element comprises an electrically resistive ribbon having a thermal time constant in still air during the preheat operation which is greater than about 15 seconds and a thermal time constant in moving air during the warming operation which is less than about 15 seconds.

The resistive ribbon may be constructed of two banks, with each bank being configured into a series of narrow channels.

Further, a shield may be provided to substantially surround the resistive ribbon, while having open opposite ends to allow air to pass therethrough.

Still further, a shield closing element, such as a mesh element may be fitted in one or both of the open opposite ends of the shield.

The invention increases the number and types of pharmaceutical formulations which can be administered efficiently and reproducibly by inhalation. More particularly, the invention makes it possible to inhale formulations which are intended for systemic delivery, including peptides such as insulin and analogs of insulin (e.g., insulin lispro). This is done by increasing the reproducibility of dosing by adjusting particle diameter to a consistent level in different surrounding humidities. Further, particular areas of the lung are targeted by (1) including aerosolized formulation in precisely determined volumes of air, (2) warming air surrounding the aerosolized formulation so as to evaporate carrier and reduce the particle diameter and/or to prevent water vapor in the air from condensing on particles, (3) excluding aerosolized formulation from other volumes of air delivered to the lung in order to correctly position an aerosol. Further, the heating means can be used with any type of means of generating an aerosol. More specifically, the heating means can be used with a nebulizer, a dry powder inhaler or metered dose inhaler. However, the major benefits of the invention are obtained when used with a device which creates aerosolized particles by moving liquid (aqueous or ethanolic) formulations through small holes to create particles (see U.S. Pat. No. 5,718,222 issued Feb. 17, 1998). All types of nebulizers benefit from the invention by reducing variable effects caused by the environment, e.g., changes in humidity.

The amount of energy added can be adjusted depending on factors such as the desired particle diameter, the amount of the carrier to be evaporated, the water vapor content (humidity) and temperature of the surrounding air, the composition of the carrier, and the region of the lung targeted.

To obtain reproducible, efficient systemic delivery it is desirable to get the aerosolized formulation deeply into the lung. This requires the delivery of the formulation in aerosol particles of diameter less than approximately 3.5 $\mu$m. Direct generation of particles in this diameter range can be difficult, due to the large ratio of surface area to volume of these small particles. Energy may be added in an amount sufficient to evaporate all or substantially all of the carrier from an aqueous aerosol and thereby provide particles of dry powdered drug or highly concentrated drug formulation to a patient which particles are (1) uniform in diameter regardless of the ambient humidity and temperature (2) preferably produced from a liquid formulation, and (3) smaller due to the evaporation of the carrier.

A primary object of the invention is to provide an air temperature controlling device comprised of a receptacle for holding a self-contained power source such as electric power cells forming a battery, a channel comprising an air flow path which includes an opening into which air can be inhaled and a second opening into which air is delivered and aerosol is generated, a heating element connected to the electrical contacts of the receptacle and positioned in a manner such that air flowing by the heating element flows through the channel, wherein the device is a hand-held, self-contained device having a total weight of one kilogram or less.

An important advantage of the invention is that the heating device can heat a sufficient amount of air so as to evaporate a sufficient amount of carrier on aerosolized particles to make the particles consistent in diameter and sufficiently small as to improve the repeatability and efficiency of drug delivery.

It is an object of this invention to provide a portable air temperature controlling device able to warm the air which will interact with particles of an aerosolized drug formulation.

It is a further object of the invention to provide a drug delivery device containing such a heating element which is heated by a portable, self-contained energy source.

It is a further object of the invention to provide methods of administering aerosolized drug formulations in which the air, interacting with or to interact with the aerosolized formulation, is warmed using a portable air temperature controlling device.

An advantage of the present invention is that it can be used for ambulatory patients.

Another object of the invention is that it makes it possible to adjust particle diameter by adding energy to the air surrounding the particles in an amount sufficient to evaporate carrier and reduce total particle diameter.

Another object of the invention is that it reduces or eliminates the variability in particle diameter due to variations in ambient relative humidity and temperature by ensuring that the delivered particles are in the range of 1–3.5 $\mu$m independent of ambient conditions. This object of the invention can apply equally well to aerosol generation devices that generate aerosols of liquid solutions of drug, liquid suspensions of drug, or dry powders of drug.

Another object is to provide a device for the delivery of aerosols which measures ambient humidity via a solid state hygrometer, and/or measures ambient temperature via a temperature sensor.

A feature of the invention is that drug can be dispersed or dissolved in a liquid carrier such as water and dispersed to a patient as dry or substantially dry particles.

These and other objects, advantages and features of the present invention will become apparent to those skilled in the art upon reading this disclosure in combination with drawings wherein like numerals refer to like components throughout.

DETAILED DESCRIPTION OF THE PREFERRED EMBODIMENTS

Figure 1:
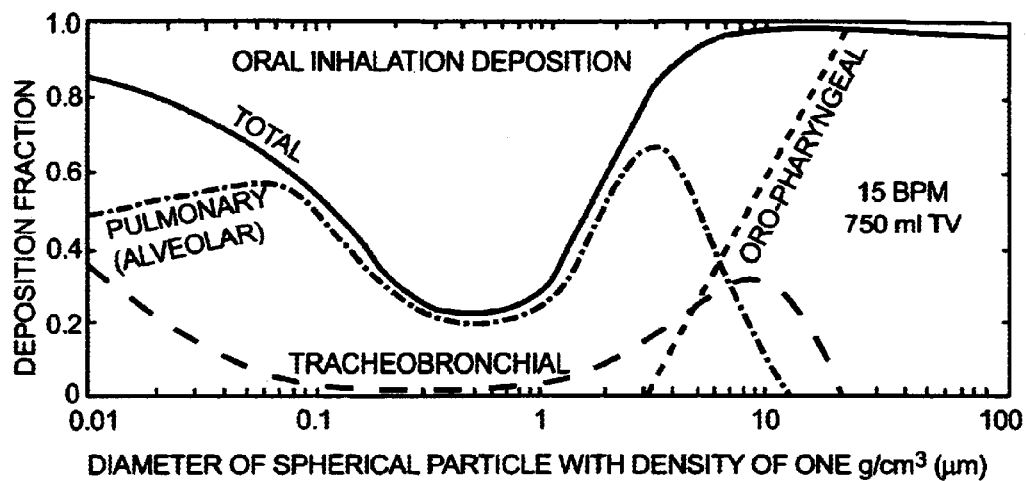
FIG. 1 is a graphic model showing the fraction of particles that deposit in the pulmonary, tracheobronchial, and oropharyngeal compartments, as a function of particle diameter.

Before the present air temperature controlling device, method of aerosolizing formulations and devices and formulations used in connection with such are described, it is to be understood that this invention is not limited to the particular embodiments described, as such heating elements, methods, devices, packages, containers and formulations may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural referents unless the context clearly dictates otherwise. Thus, for example, reference to "a formulation" includes mixtures of different formulations, reference to "an aerosolized compound" includes a plurality of such compounds, and reference to "the method of treatment" includes reference to equivalent steps and methods known to those skilled in the art, and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the specific methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The terms "portable air temperature controlling device", "air temperature controller" and the like refer to a self-contained device comprising a heating element which can be positioned in an aerosol delivery device in a manner such that air of an aerosol created by the device is warmed when contacting the heating element. The device preferably includes a receptacle for a power source for the heating of the heating element, and a control circuit to monitor and control the temperature of the heating element.

The term "receptacle" refers to a location in a portable drug delivery device for connecting a portable power source which power source is preferably two or more electric cells, i.e. a battery. The air temperature controlling device is preferably an integral part of an aerosol delivery device which together (with the power source) weigh less than 1.5 kg; more preferably, less than 0.75 kg. The receptacle may consist of an attachment point essentially outside of the device, or preferably an enclosed volume with a door that contains the power source inside the device. The receptacle preferably contains a method of connecting and disconnecting the means of transmitting power from the power source to the air temperature controlling device, such as electrical contacts.

The term "portable power source" refers to any source capable of generating power which can be transferred to the heating element in the portable air temperature controlling device, and preferably is a source of electrical energy, more preferably stored in a chemical cell which is an electric cell (two or more electric cells combined forms a battery) with or without the use of one or more capacitors in conjunction therewith. In a preferred embodiment the power source is one or more electrical cells, (i.e. a battery) which is/are sufficiently small such that when loaded into the device the device remains easily portable, e.g., AA size, C size or D size or smaller. Chemical reactions (especially the catalytic combustion of butane), hand-powered generators or friction devices could also be used.

The term "heating element" refers to any element capable of converting power provided by a portable power source into heat, storing the heat and then subsequently releasing it to the surrounding air. However, during storage, the heat energy may be distributed within the heating element. For example, a first element may be heated and the heat energy generated may be transferred into a secondary element for storage. Heating elements can be in the form of an electrically resistive material, such as one or more wires, stamped and/or folded sheets, ribbons or mesh, for example. The heating element is generally made of metal, although the present invention is not limited thereto, as heating elements made from other non-metallic materials exhibiting the desired characteristics as described herein may also be used. If the source of power is an electric cell or group of electric cells (a battery), the heating element must be designed so that its operation is consistent with a battery which is portable (size and weight are small) and can provide enough energy over a short period of time (e.g., one minute or less) to heat the heating element so that the air temperature controller holds enough energy to warm the air into which the aerosol is generated sufficiently to evaporate the desired amount of carrier away from the particles.

The terms "preheat" and "preheating" refer to the period of time and a process during which the heating element is heated from an initial temperature up to an operating temperature.

The terms "air warming", "air warming operation" and "air warming period" refer to the period of time commencing on or after achieving the operating temperature and after preheat, and during which stored heat is transferred from the heating device to air flowing through the channel that houses the heating element and any other components involved during the preheat.

The term "operating temperature" refers to a predetermined temperature at which time energy stored by the heating element during preheat may be released to air flowing into a channel of a device according to the present invention. The operating temperature, although predetermined, may vary according to the substance to be delivered by the device, the ambient temperature, the ambient humidity, and among other factors, as described in more detail below.

The term "thermal time constant" is a measure of the response time of cooling of the temperature controlling device and is a measure of the time it takes the heating device to cool from the operating temperature to a temperature equal to the sum of the initial temperature (e.g., usually ambient temperature) and 1/e of the difference between the operating temperature and the initial temperature, in the absence of any additional energy input thereto.

The "thermal time constant in moving air" refers to the thermal time constant of the heating device as air flows over the heating element as a result of inhalation by a patient or other operational driver of the airflow.

The term "thermal time constant in still air" refers to the thermal time constant in the absence of air flow, and where the air surrounding the heating element is substantially motionless.

The terms "hormone," "hormone drug," "pharmaceutically active hormone formulation," "peptide used in endocrine therapy," "peptide hormone drug," "peptide drug" and the like are used interchangeably herein. A hormone drug as described herein is a peptide drug which has been prepared in a pharmaceutically effective formulation and is useful in endocrine therapy. Specifically, a peptide drug of the type described herein is useful for exogenously modifying the behavior of a patient's endocrine system. Peptide drugs which are used in the present invention include those listed in Table 2, it being noted that these peptides preferably contain less than 50, more preferably less than 27, amino acids. Drugs of smaller size are preferred. Particularly useful peptide drugs for use with the invention include leuprolide, calcitonin, and nafarelin. The devices and methods disclosed herein can be used in the creation of an aerosol for inhalation into the lungs using any pharmaceutically active peptide. Examples of useful peptides include:

TABLE 2

Insulin (e.g. human recombinant)
Insulin analogs (e.g. insulin lispro)
Interferon-alpha
Interferon-gamma
HPTH (human parathyroid hormone)
GCSF (granulocyte colony stimulating factor)
GMCSF (granulocyte macrophage colony stimulating factor)
Atrual natriuretic factor
Angiotensin inhibitor
Renen inhibitor
Somatomedin
FSH (follicle stimulating hormone)
Tissue growth factors (TGF's)
Endothelial growth factors
HGF (hepatocyte growth factor)
Amylin
Factor VIII
Vasopressin
IIB/IIIA peptide antagonists The invention is intended to cover such pharmaceutically active peptides, which are synthetic, naturally occurring, glycosylated, unglycosylated, pegylated forms and biologically active analogs thereof. The invention can be applied to the aerosolized delivery of insulin and insulin analogs, particularly any monomeric insulin (e.g. insulin lispro).

The terms "drug", "pharmaceutically active drug", and "active drug" and the like are used interchangeably herein to refer to any chemical compound which, when provided to a mammal, preferably a human, provides a therapeutic effect. Preferred drugs are peptide hormones, proteins such as erythropoietin, peptides and the like including insulin and insulin analogs such as insulin lispro, small molecule drugs including morphine, fentanyl, and the like, i.e. drugs which are commonly used and which are conventionally delivered by injection.

The term "treatment" is used here to cover any treatment of any disease or condition in a mammal, particularly a human, and includes:

(a) preventing the disease or condition from occurring in a subject which may be predisposed to the disease but has not yet been diagnosed as having it;

(b) inhibiting the disease or condition, i.e. arresting its development; and/or (c) relieving the disease or condition, i.e. causing regression of the disease and/or its symptoms.

The term "dosing event" shall be interpreted to mean the administration of a drug to a patient in need thereof by the intrapulmonary route of administration which event may encompass one or more releases of drug formulation from a drug dispensing device over a period of time of 15 minutes or less, preferably 10 minutes or less, and more preferably 5 minutes or less, during which period an inhalation or multiple inhalations are made by the patient and a dose of drug is released and inhaled. A dosing event shall involve the administration of drug to the patient in an amount of about 1 μg to about 10 mg. The dosing event may involve the release of from about 1 μg to about 100 mg of drug from the device.

The term "bulk flow rate" shall mean the average velocity at which air moves through a channel considering that the flow rate is at a maximum in the center of the channel and at a minimum at the inner surface of the channel.

The term "carrier" shall mean any non-active compounds present in the formulation. The carrier is preferably a liquid, flowable, pharmaceutically acceptable excipient material which the pharmaceutically active drug is suspended in or more preferably dissolved in. Useful carriers do not adversely interact with the drug or packaging and have properties which allow for the formation of aerosol particles preferably having a diameter in the range of 0.5 to 15 microns. The particles may be formed when a formulation comprising the carrier and drug is forced through pores having a diameter of 0.25 to 3.0 microns. Preferred carriers include water, ethanol and mixtures thereof. Other carriers can be used provided that they can be formulated to create a suitable aerosol and do not adversely effect the drug or human lung tissue. The term carrier includes excipient materials which are used with formulation for nebulizers, any powder inhalers and metered dose inhalers or devices of the type described in U.S. Pat. No. 5,709,202.

The term "inspiratory volume" shall mean a measured, calculated and/or determined volume of air passing a given point into the lungs of a patient assuming atmospheric pressure ±5% and a temperature in the range of 10 C. to 40 C.

The terms "formulation" and "liquid formulation" and the like are used herein to describe any pharmaceutically active drug by itself or with a pharmaceutically acceptable carrier. A formulation could be a powder, that may have previously been spray dried, lyophilized, milled, or the like, and may contain a large amount of inactive ingredients such as lactose or mannitol. The formulation is preferably in flowable liquid form having a viscosity and other characteristics such that the formulation can be aerosolized into particles which are inhaled into the lungs of a patient after the formulation is aerosolized, e.g. by being moved through a porous membrane. Such formulations are preferably solutions, e.g. aqueous solutions, ethanolic solutions, aqueous/ethanolic solutions, saline solutions, microcrystalline suspensions and colloidal suspensions. Formulations can be solutions or suspensions of drug in a low boiling point propellant or even dry powders. Dry powders tend to absorb moisture and the invention decreases the moisture content and makes it possible to deliver particles of powder which have a consistent diameter even when the surrounding humidity is variable.

The term "substantially dry" shall mean that particles of formulation including an amount of carrier (e.g. water or ethanol) which is comparable to (in weight) or less than the amount of drug in the particle. Preferably such particles consist essentially of only drug with no free carrier e.g., no free water, ethanol or other liquid.

The terms "aerosol," "particles," "aerosol particles," "aerosolized formulation" and the like are used interchangeably herein and shall mean particles of formulation comprised of pharmaceutically active drug and carrier which are formed for aerosol delivery, e.g. upon forcing the formulation through a nozzle which nozzle is preferably in the form of a flexible porous membrane or generated using a jet or ultrasonic nebulizer. Preferably, the particles have a diameter in the range of 0.5 micron to about 12 microns (more preferably 1–3.5 microns).

The terms "particle diameter" and "diameter" are used when referring to the diameter of an aerosol particle and are defined as the "aerodynamic diameter". The "aerodynamic diameter" is the physical diameter of a sphere of unit density (1 gm/cm$^3$) that has the same terminal sedimentation velocity in air under normal atmospheric conditions as the particle in question. This is pointed out in that it is difficult to accurately measure the physical diameter of small particles using current technology and because the shape may be continually changing. In addition, the deposition of aerosol particles in the bronchial airways of a human subject is described by a Stokes impaction mechanism which is characterized by a particle's aerodynamic diameter. Thus, the diameter of one particle will be said to have the same diameter as another particle of the same or different material if the two particles have the same terminal sedimentation velocity in air under the same conditions.

The terms "ambient conditions," "ambient temperature," "ambient relative humidity" refer to the conditions of the air surrounding the patient and aerosol generation device, prior to this air being entrained into the device and being conditioned by the temperature controller.

The term "aerosol generation device" refers to any device for forming an aerosol for delivery to a human. These devices include but are not limited to systems that generate aerosols from liquid formulations, such as jet or ultrasonic nebulizers, spinning top generators, devices using an orifice or an array of orifices to form an aerosol (driven by a oscillation mechanism or not), and devices for the delivery of dry powder aerosols. Different types of aerosol delivery devices can utilize the temperature controller components described herein.

The term "drug delivery device" refers to a self contained portable device for the delivery of medication by way of inhalation. The drug delivery device preferably comprises a temperature controller component.

The term "temperature sensor" refers to an electrical component that has some measurable, repeatable property that can be used to determine the temperature of the component, and thus the temperature of some other substance which the sensor is in thermal contact with, such as a heating element or the surrounding air. The temperature sensor can be a thermocouple, a diode, or preferably a resistance device such as a thermistor or RTD.

The term "temperature coefficient of resistance" refers to the amount of change of the resistance of an electrical component. The temperature of a component can be measured by measuring its resistance, assuming it has a sufficiently large temperature coefficient of resistance over the range of temperatures of interest, the resistance changes monotonically, and its resistance as a function of temperature has previously been determined. The component could be a heating element, or a temperature sensor. If the component is a heating element, the preferred alloy is nickel-chromium, or similar alloy.

Device in General

An air temperature controlling device for use in conjunction with an aerosol generation device for the delivery of drugs via aerosol to the lung is disclosed. The device has a self-contained, portable power source included (electric cells which form a battery, or a combustible fuel together with a catalyst material, for example). The drug delivery device may include a receptacle for the self-contained power source. The receptacle may hold an electrical cell or cells in the receptacle in which case the receptacle will include electrical contacts. The temperature controlling device preferably comprises a channel which forms an air flow path having a first opening into which ambient air can be drawn and a second opening from which conditioned air can be delivered to the aerosol generation device, where the driving force for the air flow is preferably the patient's inhalation. The temperature controlling device preferably comprises a heating element which is connected to the contacts of the receptacle for the self-contained power source. In the preferred embodiment, the power source is a battery and the contacts are electrical contacts. However, the power source may be a container of a combustible fuel such as butane or propane, for example, in which case the contacts would be a means of connecting the power source to the means of delivering the combustible fuel to the heating element.

The heating element is positioned in a manner such that air flowing through the air flow path contacts the heating element and is warmed. In the case of a liquid formulation, the air is warmed to the extent that it can hold all or part of the carrier in the particles after it has been cooled by the process of carrier evaporation (see FIGS. 12 and 13), under all ambient conditions expected to be encountered over the lifetime of the device. In the case of a dry powder inhaler, the air is warmed to the extent that particle growth is inhibited at all ambient conditions expected to be encountered over the lifetime of the device. Preferably, the air is warmed in an amount such as to result in the evaporation of 50% or more of any liquid carrier and more preferably warmed to the extent to evaporate substantially all the compound liquid carrier leaving the particles dry, i.e. leaving the particles in a form where any liquid carrier such as water and/or ethanol which is not complexed with or bound to the solute has been evaporated away. The device is a hand-held, self-contained device which has a total weight of 1 kilogram or less in its loaded form.

The aerosol generation device to be combined with the present invention is preferably loaded with a disposable drug container of the type disclosed within U.S. Pat. No. 5,497,763 issued Mar. 12, 1996—see also U.S. Pat. No. 5,544,646 issued Aug. 13, 1996, U.S. Pat. No. 5,660,166 issued Aug. 26, 1997, U.S. Pat. No. 6,131,570, issued Oct. 17, 2000, and U.S. Pat. No. 5,718,222 issued Feb. 17, 1998, all of which are incorporated herein by reference to disclose an aerosol generation device and a disposable container for containing a drug for aerosolized delivery.

Different embodiments of the air temperature controlling device of the present invention may contain a variety of different power sources provided the power source is self-contained allowing the device to be hand held and portable. The power source may be an electric cell or a plurality of electric cells, i.e. a battery. Typically, a receptacle holds a battery securely in place and has electrical metal contacts to contact a positive and negative end of an electric cell or battery, although it would be possible to mount one or more batteries to the device and electrically connecting the batteries to a heating element without using a receptacle. Different types of batteries can be used including rechargeable batteries. It is preferable to use standard size cells, more preferably AA (or similar) size cells. Specifically, the present invention has been developed so that it is very light weight and portable and can provide the necessary warming by power received from a few AA size electric cells, or less. However, the invention is intended to encompass portable devices which include somewhat larger electric cells, e.g. D size electric cells or smaller.

The power source is brought into contact with electrical contacts (in the battery powered embodiments) on the receptacle, or otherwise electrically connected to the drug delivery device, thereby powering the drug delivery device. The electrical contacts of the receptacle lead to the heating element which is the most important aspect of the present invention and to other components of the device which require power.

The utility of the invention can be heightened by improving the efficiency of the air temperature controlling device, thus minimizing the number of batteries (and thus the size and weight of the drug delivery device), and maximizing the number of doses delivered before the power source needs to be replaced or recharged. The efficiency of the air temperature controller can be increased by insulating the walls of the air path, thus minimizing the amount of heat lost during the preheat and storage phases of the cycle. Additionally, a valving means can be used to only deliver conditioned air during the period of aerosol generation, and deliver ambient air during the parts of an inhalation prior to and following aerosol generation, thus minimizing the amount of preheating of the heating element required, and saving heat in the heating element for subsequent inhalations.

The heating element may take a variety of different forms. This form is one key feature in the design of an efficient heating mechanism that will minimize heat losses during preheating (i.e., efficiently store heat), but will maximize the release of heat to the air during an air warming operation. Although the functions of storing and releasing heat are fundamentally contradictory, the present inventors have developed distinct approaches to improving the efficiency of each of these respective functions.

The present invention provides arrangements which emphasize the dominant and distinct heat transfer mechanisms for preheating/storing of heat and releasing of heat at the particular times during which each function is being performed. More specifically, arrangements are provided which are designed to substantially eliminate or minimize convective and radiative heat transfer during preheating, while enhancing or maximizing the ability to transfer heat convectively as the air passes over the heating element. These arrangements provide systems in which the heating element is characterized by a relatively long (i.e., greater than 15 seconds) thermal time constant during preheating, but is characterized by a much shorter (i.e., less than 15 seconds) thermal time constant during release of the heat to the air during an air warming operation. A large ratio of the preheat thermal time constant (i.e., thermal constant in still air) to heat release thermal time constant (i.e., thermal constant in moving air) is a critical feature for a portable device of the type described herein. For example, in a battery embodiment, the amount of power required to heat the air directly from the batteries during aerosol formation typically far exceeds the amount of power that a portable battery pack can supply.

A heating element according to the present invention may be an electrically resistive element which, when electrically connected to a battery power source will store heat upon the dissipation of power from the battery source to the resistive element, and will subsequently release the stored heat to an air stream driven by inhalation by a patient using a device connected to the heating element. An electrically resistive element may take the form of one or more wires, stamped and/or folded sheets, ribbons, foams, meshes, or other geometry adapted to meet the thermal time constant requirements set forth above. The electrically resistive element may be formed from an alloy containing some or all of the following components: nickel, chromium, iron and copper; from pure metals or from other known electrically resistive materials capable of performing to meet the required thermal time constant characteristics. A preferred heating element is in the form of a metallic ribbon that provides a large surface area to mass ratio, most preferably a nichrome ribbon Alternatively, the heating element may be formed of metallic foam, such as nichrome foam, for example; electrically conductive mesh; metallic or other conducting wires that meet the performance described herein; gold coated wire or wires; gold coated ribbon, foam, mesh or shim stock; for example.

The composition and physical structure of the heating element must be carefully designed in order to provide a heating element which can quickly store energy in the form of heat and thereafter quickly release that stored heat energy to the surrounding air. In addition, the heating element must be such that it can perform the heat storage and release tasks when being powered by a small power source such as a few AA electric cells.

The heating element must be designed so as to provide energy in the range of about 50 to 400 joules, most preferably about 250 joules (although this value will vary depending upon the volume of drug to be treated, the amount of carrier present, and the volume of air to be heated, for example) to the surrounding air in a relatively short period of time, i.e. about 0.5 to 4.0 seconds, more preferably 1–2 seconds. In order to produce such a heating element and power source wherein the device remains small and portable it has been found that it is not possible to design the system wherein the energy is provided in real time (i.e. at the same time as the aerosol is generated) from an electrical power source, due to the internal impedance of existing battery technologies. Accordingly, the power source is used to preheat the heating element which acts as a heat sink before the energy is delivered. Thus, the concept is similar to the concept of charging a capacitor in order to operate a flash on a camera. In the same manner the heat sink or heating element of the invention acts as a "heat capacitor" and stores energy from the power source until sufficient energy is stored and then delivers that stored energy to the surrounding air at a rate well beyond that which would be possible with the power source itself. Alternatively, the power may be stored in one or more electrical capacitors, and then delivered to the heating element (or elements) from the capacitor(s) during aerosol generation. State of the art of high capacity, high discharge rate capacitors should be used. When the patient inhales through the device air is drawn over the heating element and energy is transferred to the air, warming the air. The precise amount of air warmed and the amount which the air is warmed to can be changed using different components in the temperature controlling device, or by changing the amount of preheating of the heating element prior to aerosol generation.

Optimum performance can be achieved by limiting the density of the aerosol generated. For example, it is typical to aerosolize a volume of formulation in the range of about 1 microliter to about 100 microliters per liter of inhaled air. By making the formulation more concentrated, less energy is required per mass of drug delivered in order to evaporate away the carrier and produce smaller particles. However, when the formulation is more dilute the heat energy added can have a greater effect on reducing particle diameter. More specifically, since the more dilute solution will contain a larger amount of carrier the temperature controlling device can have a larger effect on reducing the particle diameter.

The invention preferably includes a control circuit to measure and control the temperature of the heating element. This is required to optimize the amount of preheating when, for example, the batteries are near the end of their useful lifetime. It could also monitor the temperature and relative humidity of the ambient air, and vary the amount of preheating accordingly. The control circuit may be an analog circuit, digital circuit, or hybrid analog/digital circuit, and preferably includes a microprocessor. The control circuit of the invention can be designed to add the desired amount of heat depending on the amount of carrier in the aerosol particles and (1) the density (number of aerosol particles per liter of air) of the generated aerosol (2) the diameter of the particles initially as well as (3) the diameter of the particles desired after the carrier has been evaporated away. The control of the aerosol generation device may be integrated in the same circuit, and may, for example, share the microprocessor which microprocessor may be the type disclosed in U.S. Pat. Nos. 5,404,871, 5,542,410 and 5,655,516.

The device may include a hygrometer for measuring ambient humidity and/or a temperature sensor for measuring ambient temperature. Information collected by the hygrometer and/or temperature sensor is supplied to the control circuit which determines the amount of energy to be added to the surrounding air by the heating element. As the humidity increases additional energy may be necessary in order to evaporate carrier away from the particles. In the preferred embodiment, the heating element warms the air sufficiently to evaporate essentially all of the carrier over the range of ambient conditions expected in the lifetime of the device, thus obviating the need for relative humidity/ambient temperature sensor.

In general, when the heating element is in the form of a thin nickel chromium ribbon the heating element has a weight of approximately 0.05 to 5 grams, more preferably 0.1 to 4 grams, most preferably 0.2 to 2 grams. The heating element has a surface area of about 25 to 55 cm$^2$, more preferably about 30 to 50 cm$^2$, and most preferably about 35 to 45 cm$^2$. The heating element generally is capable of transferring heat to air flowing over it in the amount of about 50 to 400 joules over a period of about 0.5 to 4 seconds, more preferably about 1.0 to 2.0 seconds. Table 3, which follows, lists acceptable ranges for values characterizing heating devices employing one or more ribbon elements as a heating element. The values for a specific example (Example) are also listed.

TABLE 3

| Component | Property | Preferable range | More preferable range | most preferable range | Example | units |
| --- | --- | --- | --- | --- | --- | --- |
| Ribbon element | Mass | 0.05–5.0 | 0.1–4.0 | 0.2–2.0 | 1.25 | grams |
| | surf area | 25–60 | 30–55 | 35–45 | 39 | cm$^2$ |
| | Thickness | 0.0005–0.010 | 0.001–0.006 | 0.002–0.004 | 0.0031 | in |
| | Resistance | 0.05–3.0 | 0.2–2.0 | 0.4–1.4 | 0.8 | ohms |
| | channel width | <.16 | <.11 | <.06 | 0.048 | in |
| Shield | Mass | 0.05–4.0 | 0.1–3.0 | 0.2–2.0 | 0.65 | grams |
| | Thickness | 0.0005–0.020 | 0.001–0.010 | 0.002–0.005 | 0.0031 | in |
| Shield Closing | Percent open area | 5–60 | 10–50 | 20–40 | 30 | % |

TABLE 3-continued

| Component | Property | Preferable range | More preferable range | most preferable range | Example | units |
|---|---|---|---|---|---|---|
| Element | Mass | 0.08–1.0 | 0.10–.75 | .15–.50 | 0.25 | grams |
| System | time constant in still air | >15 | >20 | >30 | >40 | seconds |
| | time constant in moving air | <15 | <10 | <7 | 3.5 | seconds |
| | Distance between banks of heating elements | <0.240 | <0.160 | <0.080 | 0.060 | in |
| | Distance between heating element and shield | <0.250 | <0.180 | <0.12 | .055–.110 | in |
| | heat capacity | 0.2–4.35 | 0.3–2.0 | 0.4–1.2 | 1.0 | J/°C. |
| | Distance between shield closing element and heating element | <0.250 | <0.180 | <0.12 | 0.065 | in |
| | Distance between shield and channel | <0.250 | <0.180 | <0.12 | .050–0.075 | in |

In general the heating element can include an assembly of ribbon elements.

In general, the ribbon element can be formed into grooves or channels which channel air flow therethrough during the time of aerosol formation. A convenient way of obtaining such grooves or channels is by corrugating the full length of the ribbon. The width of the channels in the formed element are preferably small enough to mitigate heat losses due to free convection during the preheat stage.

It is pointed out that the device of the present invention can be used to, and actually does, improve the efficiency of drug delivery. However, this is a secondary feature. The primary feature is the improved reproducibility of the emitted dose and particle diameter over the range of ambient conditions likely to be encountered while using the device. The air temperature controlling device aids in improving repeatability by keeping the delivered aerosol particles inside of a closely controlled diameter range.

The methodology of the invention may be carried out using a portable, hand-held, battery-powered device using a microprocessor as disclosed in U.S. Pat. No. 5,404,871, issued Apr. 11, 1995 and U.S. Pat. No. 5,450,336, issued Sep. 12, 1995 incorporated herein by reference, although the methodology is not limited to such devices, as the temperature controller device may be used with other drug delivery devices, such as those which generate an aerosol by methods other than extruding a formulation through a porous membrane. The control circuit can be additionally designed to monitor inhalation flow rate, total inhaled volume, and other parameters, and commence generation of aerosol at a predefined optimal point during the inhalation. In accordance with the example system, the drug is included in an aqueous formulation which is aerosolized by moving the formulation through a porous membrane. As noted above, the heating devices and methods of the present invention are not limited to use with this type of drug delivery device, however, and may be used in combination with other delivery devices and methods. The pre-programmed information is contained within nonvolatile memory which can be modified via an external device. In another embodiment, this pre-programmed information is contained within a "read only" memory which can be unplugged from the device and replaced with another memory unit containing different programming information. In yet another embodiment, a microprocessor, containing read only memory which in turn contains the pre-programmed information, is plugged into the device. For each of these embodiments, changing the programming of the memory device readable by a microprocessor will change the behavior of the device by causing the microprocessor to be programmed in a different manner. This is done to accommodate different drugs for different types of treatment.

The drug which is released to the patient may be in a variety of different forms. For example, the drug may be an aqueous solution of drug, i.e., drug dissolved in water and formed into small particles to create an aerosol which is delivered to the patient. Alternatively, liquid suspensions or dry powders may be used. Alternatively, the drug may be in a solution wherein a low-boiling point propellant is used as a solvent.

Some peptide drugs are subject to being degraded more quickly when in solution such as an aqueous solution. Preferably such drugs are packaged in a dry form and mixed with water prior to administration. A dual compartment container for carrying out such is shown in U.S. Pat. No. 5,672,581. Alternately, the drug is kept in the form of a dry powder which is intermixed with an airflow in order to provide for delivery of drug to the patient.

Regardless of the type of drug or the form of the drug formulation, it is preferable to create aerosol particles having a diameter in the range of about 1 to 3.5 microns. By creating particles which have a relatively narrow range of diameter, it is possible to further increase the efficiency of the drug delivery system and improve the repeatability of the dosing. Thus, it is preferable that the particles not only have a diameter in the range of 1.0 to 3.5 microns but that the mean particle diameter be within a narrow range so that 80% or more of the particles being delivered to a patient have a particle diameter which is within 50% of the average particle diameter, preferably 25% of the average particle diameter. The heating element is particularly useful in reducing particle diameter and in creating an aerosol with uniform sized particles.

The amount of drug delivered to the patient will vary greatly depending on the particular drug being delivered. In accordance with the present invention it is possible to deliver a wide range of drugs. For example, drugs delivered could be drugs which have a systemic effect e.g. leuprolide, insulin and analogs thereof including monomeric insulin, or morphine; or a local effect in the lungs e.g. Activase, albuterol, or sodium cromoglycate.

TABLE 4

Useful Peptide Hormone Drugs

| Compound | Amino acids |
| --- | --- |
| Somatostatin | 6 |
| Oxytocin | 9 |
| Desmopressin | 9 |
| LHRH | 10 |
| Nafarelin | 10 |
| Leuprolide | 11 |
| ACTH analog | 17 |
| Secretin | 27 |
| Glucagon | 29 |
| Calcitonin | 32 |
| GHRH | 40 |
| Growth hormone | 191 |

Having generally described the invention above reference is now made to the figures in order to more particularly point out and describe the invention.

FIG. 1 is a graph of deposition fraction versus particle diameter with the particle diameter being the aerodynamic diameter of a particle having a density of 1 gram per square centimeter with the scale being read in terms of increasing particle diameter in units of $\mu$m. The aerodynamic diameters are plotted versus the deposition fraction in the lungs. For each of the different lines shown on the graph the data is provided for the deposition fraction in the different areas of the lung and for the total deposition. As can be seen on the graph the oro-pharyngeal deposition which is basically in the back of the throat occurs for particles which are somewhat large. Specifically, as the particle size increases to an aerodynamic diameter above 10 $\mu$m nearly all of the particles are deposited in the oro-pharyngeal area. It is pointed out that the graph does not represent actual data but is believed to be a fairly accurate representation of what occurs during intrapulmonary drug delivery particularly where the patient being tested is breathing at a rate of 15 breaths per minute with a 750 ml tidal volume.

Figure 2:
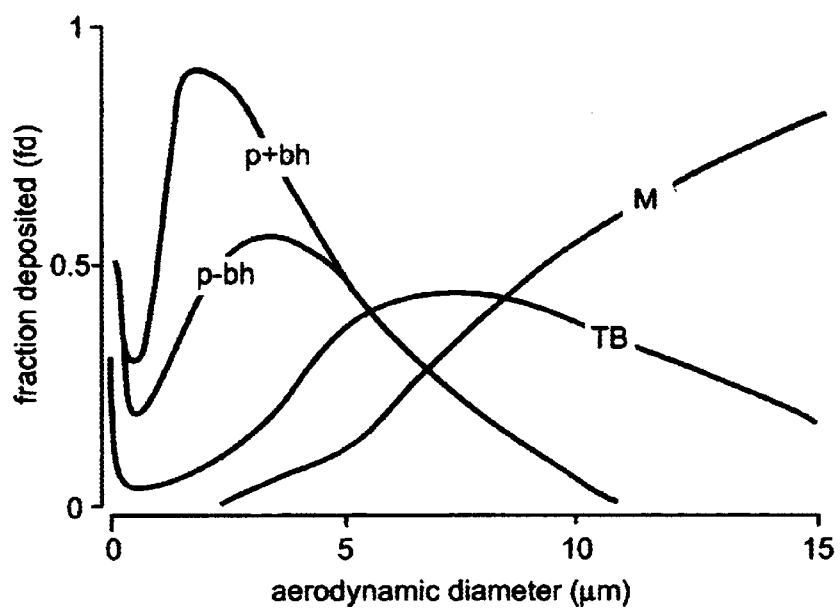
FIG. 2 is a graphic model similar to FIG. 1, showing the effect of a breath hold maneuver on lung deposition.

FIG. 2 is similar to FIG. 1 and is a plot of aerodynamic diameter versus fractional deposition. In FIG. 2 the graphs show "p" which is pulmonary deposition with "bh" breath holding and without breath holding. Similar to FIG. 1, this graph represents theoretical and not actual data. As can be seen in the graph the breath holding technique does improve the amount of pulmonary deposition, particularly when the particles have an aerodynamic diameter less than 5 $\mu$m.

FIGS. 1 and 2 together clearly indicate the importance of the present invention. Specifically, the figures indicate that the area of the lung which particles deposit in and the percentage of the particles which deposit there is substantially effected by the aerodynamic diameter of the particles. In that the present invention makes it possible to provide for consistent aerodynamic particle size the invention provides for consistent delivery of the particles to particular areas of the lung and therefore repeatable dosing of a patient.

Figure 3:
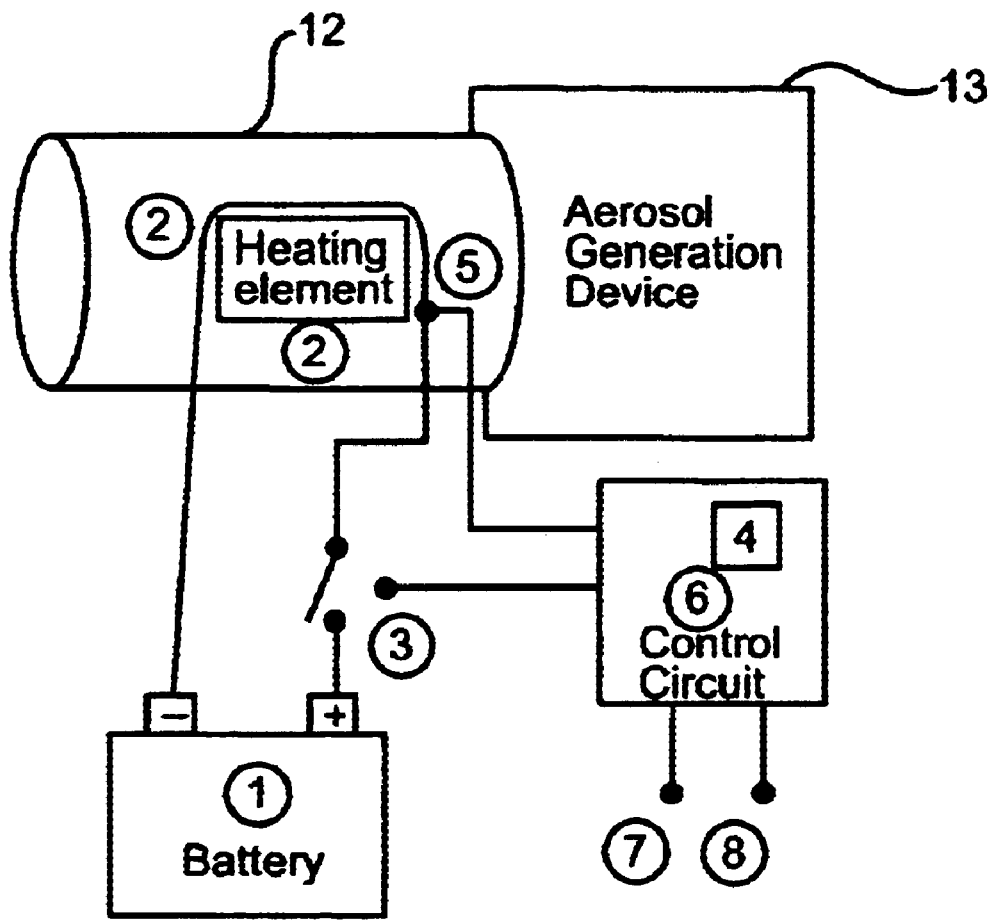
FIG. 3 is a schematic view of an embodiment of an air temperature controlling device of the invention.

FIG. 3 schematically shows an embodiment of the air temperature controller which employs a portable battery power source. Battery 1 is electrically connected to heating element 2 through relay 3. The relay 3 may be a mechanical, or preferably a solid state relay. Relay 3 is controlled by control circuit 6 which includes microprocessor 4. Temperature sensor 5 is in thermal contact with heating element 2, and is monitored by control circuit 6. Optional ambient relative humidity sensor 7 and ambient temperature sensor 8 are also monitored by control circuit 6. Ready light 9 (see FIG. 4) is controlled by microprocessor 4. Power for the entire system is supplied by battery 1. The heating element 2 is positioned in air path 11 formed by the cylinder 12, leading to aerosol generation device 13.

Figure 4:
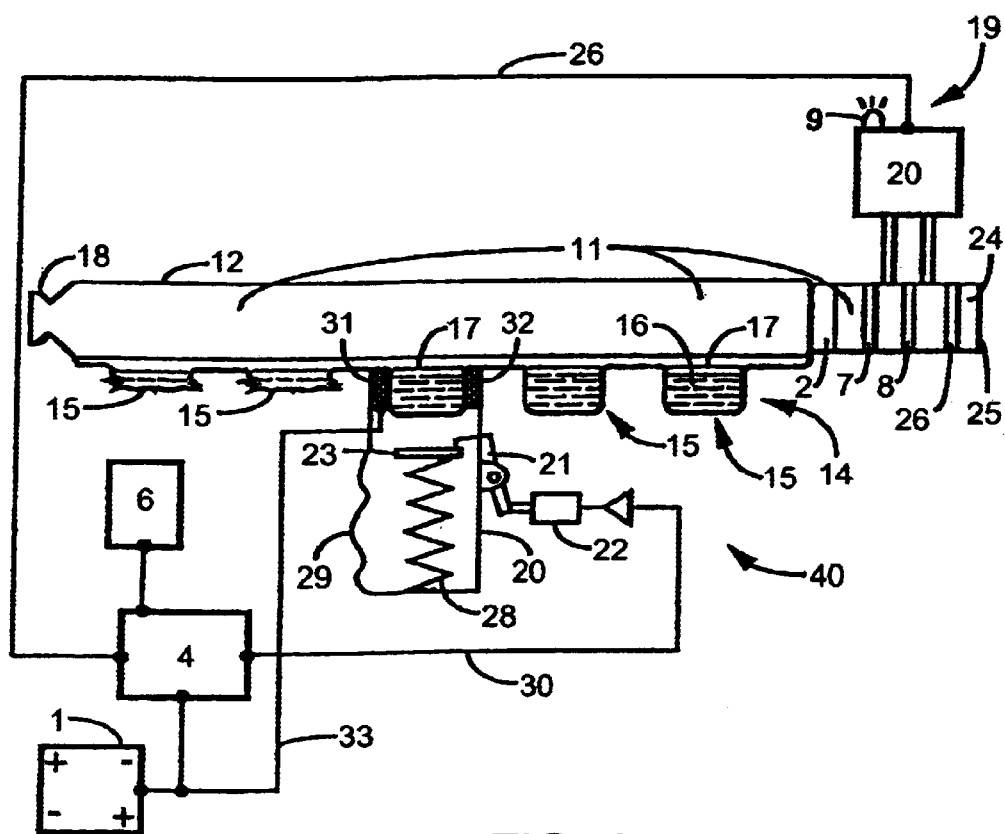
FIG. 4 is a schematic view of an embodiment of an aerosol delivery device of the invention.

FIG. 4 is an embodiment of an aerosol drug delivery device utilizing the invention. The device 40 shown in FIG. 4 is loaded with a disposable package 14. To use the device 40 a patient inhales air from the mouthpiece 18 through the opening 25 in the cylinder 12. The air drawn in through the opening 25 (and optionally the desiccator 24) flows through the flow path 11 of the channel 12. The disposable package 14 is comprised of a plurality of disposable containers 15. Each container 15 includes a drug formulation 16 and is covered by a nozzle array or porous membrane 17. The heating element 2 is located in the flow path 11. The heating element 2 is preferably positioned such that all or only a portion of the air flowing through the path 11 will pass by the heating element 2, e.g., flow vent flaps can direct any desired portion of air past the heating element 2. The relay 3 (see FIG. 3) is preferably closed for 30 sec or less prior to inhalation and opened after drug delivery to conserve power.

The device 40 may include a mouth piece 18 at the end of the flow path 11. The patient inhales from the mouth piece 18 which causes an inspiratory flow to be measured by flow sensor 19 within the flow path which path may be, and preferably is, in a non-linear flow-pressure relationship. This inspiratory flow causes an air flow transducer 20 to generate a signal. This signal is conveyed to a microprocessor 4 which is able to convert the signal from the transducer 20 in the inspiratory flow path 11 to a flow rate. The microprocessor 4 can further integrate this continuous air flow rate signal into a representation of cumulative inspiratory volume.

When the device is turned on by the user, the microprocessor 4 will send a signal to send power from the power source 1 (which is preferably a small battery) to the air temperature controller 2 and will continue to preheat the temperature controller 2 until it reaches a predetermined temperature. The preheat temperature can be preprogrammed based on such information as the particle diameter generated, the particle diameter desired, the formulation concentration, and other parameters. The microprocessor 4 may also adjust the preheat temperature to optimize each delivery based on the ambient conditions, using information from the optional hygrometer/temperature sensor 7. The microprocessor 4 also sends a signal to an actuator 22 which causes the mechanical means (e.g., the piston 23) to force drug from a container 15 of the package 14 into the inspiratory flow path 11 of the device 40 where the aerosol is formed and entrained into the inhalation air and delivered into the patient's lungs.

When the formulation 16 includes water as all or part of the carrier it may also be desirable to include a desiccator 24 within the flow path 11. The desiccator 24 is preferably located at the initial opening 25 but may be located elsewhere in the flow path 11 prior to a point in the flow path when the formulation is fired into the flow path in the form of aerosol particles. By drawing air through the desiccator 24 water vapor within the air is removed in part or completely. Therefore, only dried air is drawn into the remainder of a flow path. Since the air is completely dried, water carrier within the aerosol particles will more readily evaporate. This decreases the energy needs with respect to the temperature controller 2. The desiccator material can be any compound which absorbs water vapor from air. For example, it may be a compound selected from the group consisting of $P_2O_5$, $Mg(ClO_4)$, KOH, $H_2SO_4$, NaOH, CaO, $CaCl_2$, $ZnCl_2$, and $CaSO_4$.

Device Operation

The operation of the device 40 can be understood by reference to a combination of FIGS. 3 and 4. Referring to FIG. 3 when the relay 3 is closed the heating element 2 begins to heat. In addition to the heating element 2 present within the flow path 11 the flow path may also include a humidity sensor 7, temperature sensor 8 and electronic airflow sensor 26. When a patient (not shown) inhales through the mouth piece 18 air flows in through the opening 25 and is sensed by the air flow sensor 26 after being electronically converted by the transducer 20. The signal flows along the electrical connection 26 to the microprocessor 4. The combination of the control circuit 6 and the microprocessor 4 send a signal back through the connection 26 to the heating element 2 which is powered by the battery 1. The amount of power to be supplied to the heating element 2 is also tempered, to a degree, by information received from the humidity sensor 7 and temperature sensor 8 which information is considered by the microprocessor 4. When the heating element 2 reaches the correct temperature and the air flow sensor 26 determines that the inspiratory flow rate and inspiratory volume are at the desired point the microprocessor 4 sends a signal to the actuator 22. The actuator 22 may be any type of device such as a solenoid which then moves the mechanical release member 21 so that the piston 23 is released. The piston 23 is forced upward by a spring or other biasing means 28. The biasing means may be held within a grip 29 which can be easily held by the user. Where the microprocessor 4 sends the signal through the line 30 to the actuator 22 the spring is released and a container 15 is crushed and the formulation 16 inside the container is released through the membrane 17.

When the container 15 is present in the drug release position below the piston 23 the container 15 may have vibrating devices 31 and 32 positioned on either side or a single device surrounding the container 15. The vibrating device(s) may be actuated by the microprocessor 4 sending a signal through the connection 23. Empty containers 15 are shown to the left of the drug actuation point. In a preferred embodiment of the methodology a new container and new porous membrane are used for each drug release. By using a new porous membrane each time clogging of the porous membranes is avoided. Further, possible contamination of the formulation 16 present in the container 15 is avoided.

Those skilled in the art will recognize that a variety of different components could be used in place of some of the components shown within FIGS. 3 and 4. For example, rather than including a piston biased by a spring it would be possible to utilize a rotating cam. Also, rather than passing the formulation through a porous membrane to generate the aerosol, an aerosol could be generated by jet nebulization, ultra-sonic nebulization, spinning disk atomization, dispersion of a dry powder, and pneumatic atomization such as by swirl atomization, or air blast atomization. Further, other components of the invention, although preferred, are not required. For example, components such as the humidity sensor 7 and temperature sensor 8 could be eliminated without substantial impairment of operability by simply adjusting the amount of energy supplied to the heating element 2 so as to compensate for any humidity or temperature which might be encountered by the user. However, such would acquire the use of unnecessary amounts of power in some situations.

When the air temperature controller shown in FIG. 3 is activated, microprocessor 4 closes relay 3, commencing the preheat of heating element 2. Microprocessor 4 monitors temperature sensor 5 until heating element 2 reaches a temperature that is determined by ambient conditions as measured by optional ambient relative humidity sensor 7 and/or ambient temperature sensor 8, or preferably a temperature that has been previously determined to be sufficient for all ambient conditions to be seen in the normal operation of the device. When this temperature is reached, the microprocessor opens relay 3 to inhibit further heating, and lights the ready light 9 to signal to the patient that the device is ready for a dosing event. The microprocessor continues to monitor temperature sensor 7 and opens and closes relay 3 as required to maintain the desired temperature until the patient inhales from the device.

Heating Element and Efficiency Enhancement

Figure 5:
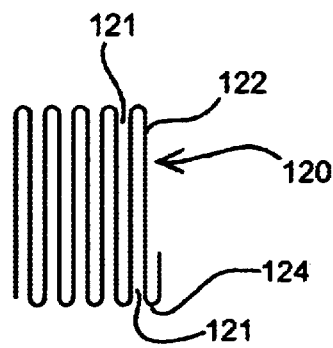
FIG. 5 is an end view of a configuration of a heating element according to the present invention.
Figure 6:
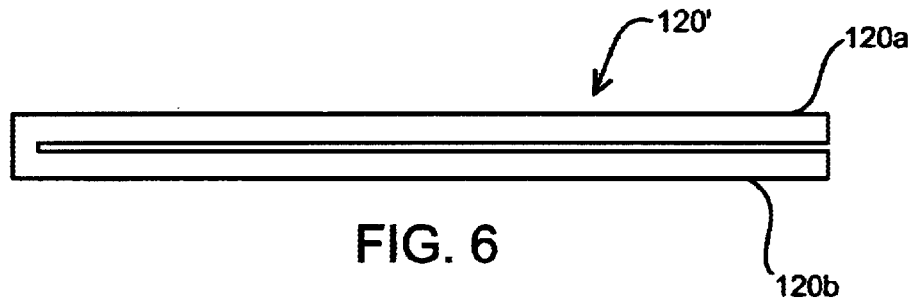
FIG. 6 is a plan view of an electrically resistive ribbon used in making a heating element according to the present invention.

FIG. 5 shows an end view of a configuration of a heating element 120 according to the present invention which is particularly useful when the amount of carrier to be evaporated is about 45 microliters in about a liter of air in less than about three seconds, more preferably 1 to 2 seconds, most preferably about 1 second, using no more than 4 AA battery cells as the power source. The largest source of inefficiency in known heating elements such as disclosed in U.S. Pat. No. 6,131,570, for example, was displayed in the energy remaining in the heating element at the end of a transfer cycle corresponding to the inhalation by a patient, during which time heat is transferred from the heating element to the air flowing over the heating element to be mixed with the aerosol. One way of improving the heat transfer efficiency of a heating element during such a transfer cycle is to increase the surface area to mass ratio of the heating element. The heating element 120 is formed from an electrically resistive ribbon 120' as shown in FIG. 6, preferably of nichrome, characterized by a significantly higher surface area/mass ratio than that of previous nichrome element embodiments, such as 24 gauge or 28 gauge wire embodiments. The surface area/mass ratio of ribbon 120' is preferably in the range of about 1.5 to 30 $in^2/g$, more preferably in the range of 3 to 20 $in^2/g$, most preferably in the range of 4 to 7 $in^2/g$. The use of ribbon is superior to simply thinning down the cross sectional area of wire because the ribbon is more rigid than wire having a similar thickness. Additionally, because its cross-sectional area can be changed by simply changing the ribbon width, a wide range of mass/resistance combinations are available for tuning the heating element to have the desired heat storage and heat transfer characteristics. Although nichrome is preferred, it is possible to use other alloys exhibiting high electrical resistivity and high resistance to oxidation at elevated temperatures, to include alloys containing copper, chromium, iron and/or nickel, for example.

The flat ribbon 120' is constructed as a two bank piece 120a, 120b (FIG. 6), and the banks are then formed into a series of narrow channels or grooves 121 by forming corresponding bends 122 and 124 in both banks. In other configurations the heating element may comprise a greater number of banks. The distance between the banks should be small to reduce preheat losses due to free convection, preferably less than 0.24 inches, more preferably less than 0.16 inches, and most preferably less than 0.08 inches. The total element length and width are selected to exhibit the desired mass and electrical resistance. The electrical resistance of the element is preferably in the range of 0.05 to 20 ohms, more preferably 0.07 to 4 ohms, most preferably 0.1 to 2 ohms. The mass of the element is preferably in the range of 0.05 to 5 grams, more preferably in the range of 0.1 to 4 grams, most preferably in the range of 0.2 to 2 grams.

The width of the channels of the corrugated ribbon is small to mitigate preheat losses due to free convection, preferably less than 0.16 inches, more preferably less than 0.11 inches, and most preferably less than 0.06 inches.

Figures 7A, 7B:
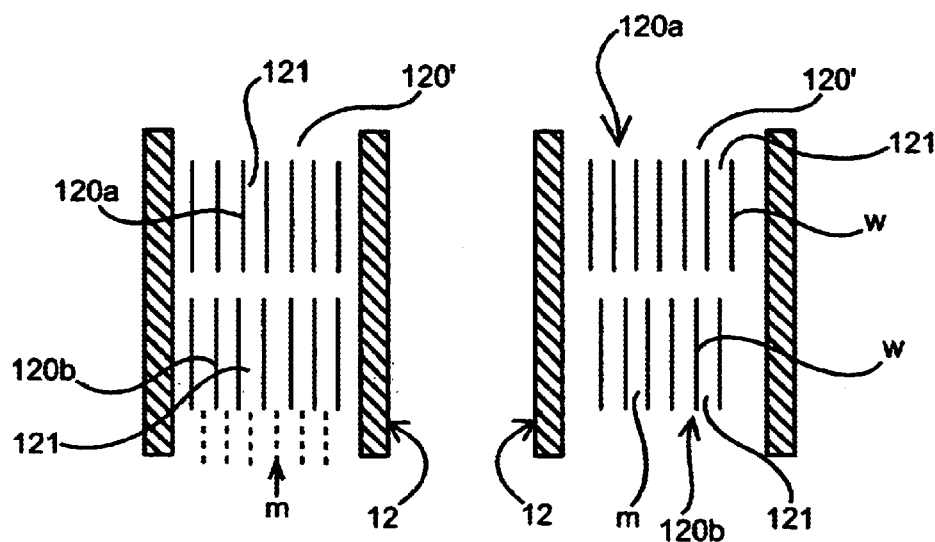
FIG. 7A is a schematic showing channels of one bank of a heating element substantially aligned with respect to the other bank.
FIG. 7B is a schematic showing channels of one bank of a heating element substantially non-aligned with respect to the other bank.

The mitigation of preheat losses due to free convection results in a more uniform temperature inside the heating element and therefore in a greater insensitivity to device orientation and sensor location. The channels of one bank with respect to the other may be, but need not be aligned with one another, as can be seen by comparing the schematic example showing aligned banks 102a. 120b in FIG. 7A with the schematic example showing non-aligned banks 102a, 102b in FIG. 7B. In fact, a misalignment can be used to increase the efficiency of heating of moving air. For example, if the channels or grooves 121 defined by the first bank 120a are aligned with those channels or grooves 121 of the second bank 120b (see FIG. 7A), the air flowing out of the first bank 102a and into the second bank 120b would be colder at the midplanes m of the channels than near the channel walls w (the ribbon surface). Instead, when the channel walls w of the first bank 120a are positioned on the planes defined by the midplanes of the channels 121 of the second bank 120b (see FIG. 7B) the air flowing into the second bank 120b is warmest in the midplanes m of the channels 121 of bank 120b. Bank 120b can also be offset from bank 120a at positions intermediate of the non-offset configuration in FIG. 7A and the offset positioning shown in FIG. 7B.

Figure 8:
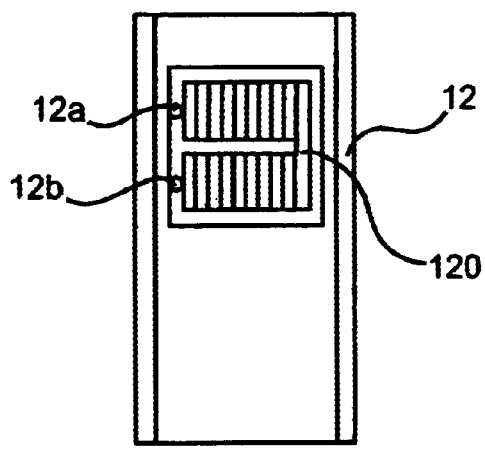
FIG. 8 is a view of a heating element mounted in a channel according to the present invention, with the view of the channel being cut away.
Figure 9:
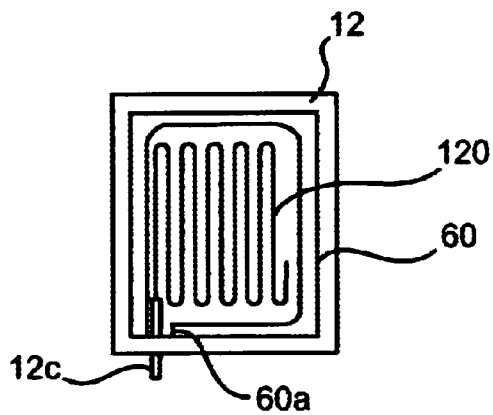
FIG. 9 is an end view of a heating element mounted in a channel according to the present invention.

The heating element may then be mounted in a channel 12, as shown in FIG. 8 with the view of channel 12 being cut away. Channel 12 may be formed from polyether ether ketone (PEEK) or other material which is preferably also stable at elevated temperatures and relatively non-thermally conducting. Penetrations 12a and 12b are formed in the channel 12 to allow the passage of electrical contacts 12c (see FIG. 9) which electrically connect the heating element with a power source. The penetrations are preferably designed such that they will secure the position of the contacts and the element while preventing air from leaking through them. Alternatively, the contacts may run through the air pathway without penetrating channel 12.

Figure 10:
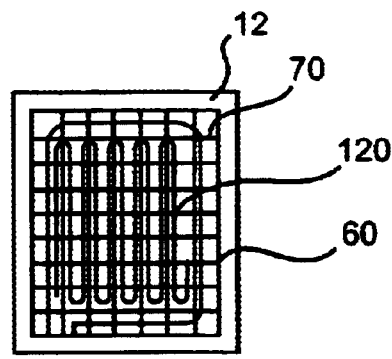
FIG. 10 is an end view of a heating element mounted in a channel and showing a mesh element fitted at the end of the channel.

A shield 60 may be (and preferably is) provided around the heating element 120, such that it closely surrounds the heating element 120, but does not touch it. The distance between the element 120 and the shield 60 is small to reduce preheat losses due to free convection, preferably less than 0.25 inches, more preferably less than 0.18 inches, most preferably less than 0.12 inches. Shield 60 may be formed of nichrome ribbon or similar material with thickness preferably in the range of 0.0005 to 0.020 inches, more preferably in the range of 0.001 to 0.010 inches, most preferably in the range of 0.002 to 0.005 inches., and completely surround the heating element on four sides and along the entire length thereof, leaving open only the ends through which air flow is channeled. The ends may be closed with shield closing elements 70 in FIG. 10, that contain open spaces to allow air to flow therethrough. Shield closing elements 70 are preferably made of wire mesh, and are thus referred to as "mesh elements", but may be made of perforated sheet metal or the like which allow flow therethrough, but also act as a shield and discourage convection during energy storage (e.g., during the preheat stage) while acting as a passive element during energy release (e.g., after operation temperature has been reached and air is flowed through the shield closing element(s) and heating element). Shield closing (mesh) elements 70 are preferably close to heating element 120 on both ends to reduce preheat losses due to free convection, preferably less than 0.25 inches, more preferably less than 0.18 inches, most preferably less than 0.12 inches. The shield 60 may be formed to have one or more tabs 60a that extend to connect with the channel 12, but this is kept to a minimum to minimize heat transfer to the channel 12. The distance between the shield 60 and the channel 12 is small to reduce preheat losses due to free convection, preferably less than 0.25 inches, more preferably less than 0.18 inches, most preferably less than 0.12 inches. Heat that is normally transferred to the surroundings (in the absence of a shield) during preheating of the heating element 120 (due to radiation and free convection) is instead transferred to the shield 60 during the preheat. Some of this heat is then recovered and transferred to the air that flows over the shield 60 and heating element 120 during an inhalation.

Meshes 70 may be formed of nichrome wire or the like, having a diameter of about 0.0005" to about 0.0100", more preferably about 0.0045" to about 0.0065", and about 5% to 60% open area, more preferably about 10% to 50% open area, and most preferably about 20% to 40% open area. Inlet plates with holes forming a similar amount of open area could alternatively be used in place of the mesh element 70 on the inlet side of the shield 60. Use of the shield closing elements 70 and shield 60 has been shown to increase the efficiency of the heating element, most likely by reducing heat losses during preheat losses (i.e., preheat losses) due to free convection and thermal radiation.

Passive elements can be introduced in the air flow path downstream from the heating element to lengthen the thermal time constant in moving air of the heating device. These are typically perforated or porous, and may be made of woven wire mesh, for example, to allow the air to pass through, although other example geometries that may be employed include corrugated members, foam and/or wire. During the early part of the air warming period, they absorb heat from the moving air, while during the late part of the air warming period they release heat into the moving air, thus lengthening the time constant. Passive elements may result in a heat transfer inefficiency because the heat that they absorb will not entirely be released to the air during the air warming operation. Therefore, the masses and geometries of the passive elements must be carefully chosen to create the desired effect without greatly reducing efficiency, and will vary depending upon the effect desired.

Figure 11:
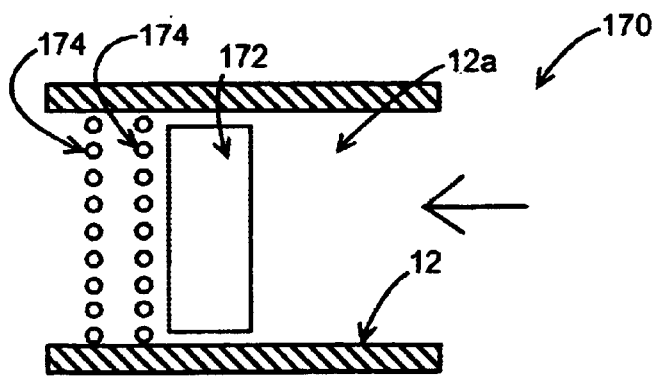
FIG. 11 shows an arrangement employing a passive element to lengthen the time constant in moving air of the heating device.

An example of a passive heating element 174 is shown in FIG. 11. FIG. 11 shows an arrangement which lengthens the time constant of the heating device for better matching of the heat pulse developed thereby to the aerosol being generated. One or more passive elements 174 are situated downstream of one or more heating elements 172 (which may be of a ribbon type 120 or other configuration as described herein) in heating device 170. During the early part of the air warming period the passive element(s) 174 absorb(s) heat from the moving air having flowed past heating element(s) 172 (in the direction of the arrow in FIG. 11) and warmed thereby. During the later part of the air warming period, the passive element(s) 174 release(s) heat into the moving air, thus lengthening the time constant in moving air of the overall heating device.

Another way of increasing efficiency in a temperature controlling device is to apply a gold coating over the heating element and/or shield and/or shield closing element(s). The emissivity of gold is very low (i.e., 0.02) compared to materials used for making the heating element, shield and shield closing elements. For example, the emissivity of nichrome is about 0.8. Thus, by sputtering a very thin layer (on the order of a few atoms thick) of gold over one or more of the previously mentioned components, increases in efficiency in storing heat of about 10% have been achieved.

As noted above, the heating devices described above are configured to be powered electrically, such as by batteries, so as to be portable. For example, to power a system including a heating device in combination with a delivery device, five AA-sized Nickel Metal-Hydride cells (or less, e.g., two, three, four) are connected in series to give a battery voltage of about 5 V. The cells each have a capacity of about 1.3 Ahr.

Energy for Evaporation

Figure 12:
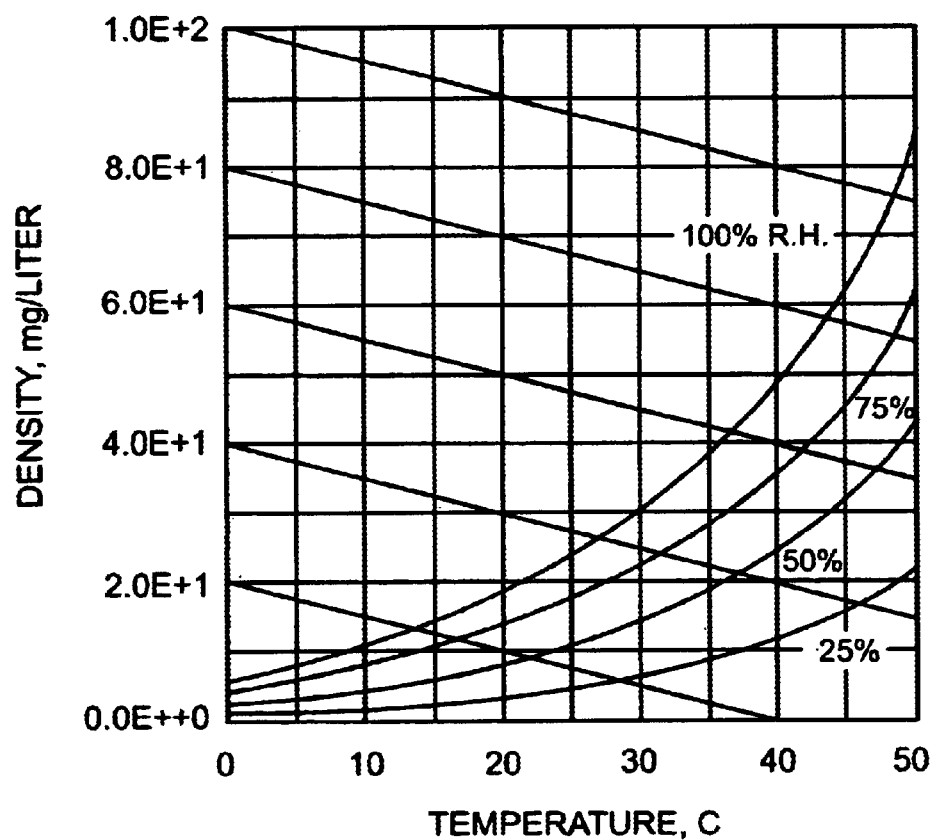
FIG. 12 is a graph plotting the density (mg/liter) of water vapor in air versus temperature.

FIG. 12 is a graph which can be used in calculating the amount of energy needed to control the diameter of delivered droplets by controlling the amount of evaporation of carrier from the aerosolized droplets. The graph of FIG. 12 contains two types of information, the density of evaporated water vs. temperature and relative humidity, and the cooling of the air as the water evaporates. The four lines that show a rapid increase with temperature portray the density of water vapor in air, at 25, 50, 75, and 100% relative humidity, respectively. The 100% relative humidity curve represents the maximum number of milligrams of water that can be evaporated per liter of air. The diagonal lines show the temperature change of the air as the water droplets evaporate (hereafter called the air mass trajectory curves). As the evaporation proceeds, the density and temperature will change by moving parallel to these curves. To calculate these curves, air density of 1.185 grams/liter, air specific heat of 0.2401 calories/gram, and water latent heat of vaporization of 0.583 cal/mg were assumed. It is also assumed that the evaporation process is adiabatic, i.e. there is no heat removed from or supplied to the air from other sources such as the walls of the device. These values imply that a liter of air will cool 2 degrees Celsius for every milligram of water evaporated, i.e. evaporating 10 microliters will cool a liter of air 20 degrees Celsius.

FIG. 12 can be used to calculate the amount of preheating needed to evaporate all or substantially all of the carrier in the aerosol particles. As an example, assume the initial ambient conditions are 25° C. and 50% relative humidity. Further, assume that one wants to evaporate 10 $\mu$l (10 mgs) of water from an aqueous drug solution. Finally, assume the final relative humidity is 75%. Under these conditions the aqueous carrier would not in general evaporate completely. More specifically, the final particles would contain approximately equal amounts of drug and water. To calculate the amount of energy to add for this delivery maneuver, refer to FIG. 12. Locate the point corresponding to 25 C. and 50% relative humidity. Move up by 10 milligrams, the amount of water to be evaporated. Now move to the right until the 75% RH curve is crossed. This occurs at about 29 C. These conditions (75% RH and 29 C.) represent the condition of the air as delivered to the patient. However, still more energy must be added to make up for the cooling of the air as the water evaporates. To calculate this amount of heat, move parallel to the air mass trajectory curves (downward and to the right) until the initial ambient water vapor density is reached, at approximately 47 C. Thus, sufficient heat to warm the air by 22 C. must be added to achieve near complete evaporation.

Figure 13:
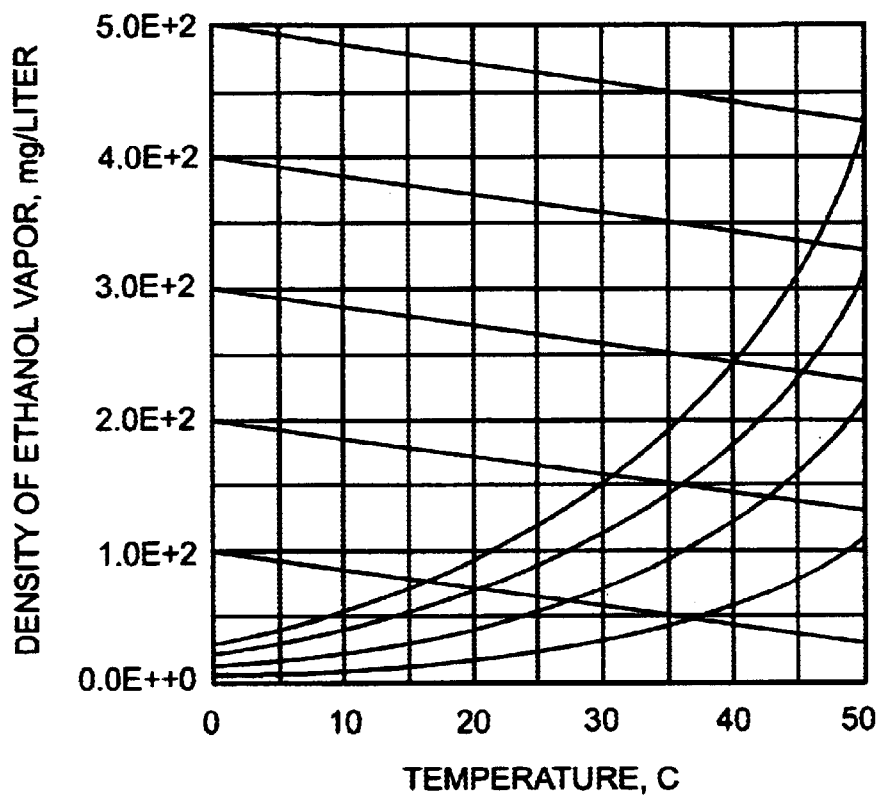
FIG. 13 is a graph plotting the density (mg/liter) of ethanol vapor in air versus temperature.

FIG. 13 includes similar information with respect to ethanol which can be used in a similar manner. A preferred embodiment of the invention comprises a microprocessor programmed to calculate the amount of energy needed for the formulation being aerosolized with consideration to the surrounding temperature and humidity being accounted for. In a preferred embodiment, containers of formulation loaded into the device are labeled in a manner which is read by the device which then considers the diameter of the formulation dose to be aerosolized and the amount of liquid to be evaporated.

The evaporation and growth rates of aqueous droplets is a function of their initial diameter, the amount of drug dissolved therein (concentration) and the ambient relative humidity and temperature. The determining factor is whether the water vapor concentration at the surface of the droplet is higher or lower than that of the surrounding air. Because the relative humidity at the surface of a particle (i.e. droplet of aerosolized formulation) is close to 100% for most formulations of interest, evaporation will occur under most ambient conditions until the rising humidity of the air equals the decreasing humidity at the surface of the droplet. A five micron droplet is expected to evaporate to a 1 micron dry particle in 0% humidity in less than 20 ms.

When administering drug using the inhalation device of the present invention, the entire dosing event can involve the administration of anywhere from 10 $\mu$l to 1,000 ml of drug formulation, but more preferably involves the administration of approximately 15 $\mu$l to 200 $\mu$l of drug formulation. Very small amounts of drug (e.g., nanogram or larger amounts) may be dissolved or dispersed within a pharmaceutically acceptable, liquid, excipient material to provide a liquid, flowable formulation which can be readily aerosolized. The container will include the formulation having drug therein in an amount of about 10 $\mu$g to 300 mg, more preferably about 1 mg. The large variation in the amounts which might be delivered are due to different drug potencies and solubilities and different delivery efficiencies for different devices, formulations and patients.

System Specification Envelope

The following information is provided to specify an approximate envelope for the design of various features of a temperature controlling system according to the present invention.

A. Batteries
  Chemistry: Nickel Cadmium, Nickel Metal-Hydride, Lithium-Ion, Lithium-Metal, Lithium Polymer
  Voltage: 1 Volt to 20 Volt
  Internal Impedance: less than 0.1 Ω per cell
  Number of cells: 1 to 10
B. Control Relay
  Type: Solid State, Mechanical, Transistor
C. Temperature Sensors
  Types: Resistance, Thermocouple, Diode The following example is put forth so as to provide those of ordinary skill in the art with a complete disclosure and description of how to make and use various constructs and perform the various methods of the present invention and are not intended to limit the scope of what the inventors regard as their invention nor are they intended to represent or imply that the embodiments described below are all on the only embodiments constructed or tested. Efforts have been made to ensure accuracy with respect to numbers used (e.g., amounts, concentrations, particular components, etc.) But some deviations should be accounted for.

EXAMPLE

One example of a heating device according to the present invention is characterized in Table 3 above and employed a ribbon type heating element as described above, with the heating device being powered by 4 AA NiMH battery cells arranged in series. The ribbon was made from a nichrome alloy (80% nickel, 20% chromium), had a mass of about 1.2 g., a surface area of about 39 $cm^2$ and a thickness of about 0.0031 inches, and was formed to have two banks like that described with regard to FIG. 6 above. The channel or gap width between folds of the heating element was about 0.048 inches and the distance between banks (as described with regard to FIGS. 6 and 8 above) was about 0.060 inches. The heating element exhibited an electrical resistance of about 0.8 ohms and a heat capacity of about 0.5 J/° C. A shield 60 (as shown and described with respect to FIG. 9) surrounded the ribbon element and had a mass of about 0.65 grams and a thickness of about 0.0031 inches. The distance between the shield 60 and the ribbon element was about 0.055 to 0.110 inches on average. A shield closing element 70 was fitted in each open end of shield 60 and each comprised a mesh element having about 30% open area and a mass of about 0.25 grams. The distance between the shield closing elements or mesh elements and the ribbon element was about 0.065 inches for each. The distance between the shield 60 and the channel 12 was about 0.050 to 0.075 inches. The thermal time constant in still air of this heating device was greater than about 40 seconds. The thermal time constant in moving air of this heating device was measured to be about 3.5 seconds at an air flow rate of about 45 l/min, which was an air flow rate designed to model an inspiratory flow rate of a patient.

The invention as shown and described is considered to be the one of the most practical and preferred embodiments. It is recognized, however, that the departures may be made therefrom which are within the scope of the invention and that obvious modifications will occur to one skilled in the art upon reading this disclosure.

What is claimed is:

1. A method of dissipating power to store heat in a heating element of a temperature controlling device, and then releasing the stored heat to warm air for evaporating a composition containing a pharmaceutically active formulation, said method comprising the steps of:
    supplying power from a portable power source to a heating element, said device having a long thermal time constant in still air of greater than about 10 seconds;
    storing heat in the heating element as power is supplied from the portable power source;
    determining when the heating element achieves a predetermined operating temperature; and
    flowing air over the heating element after the heating element has achieved the predetermined operating temperature, to release heat to the flowing air, whereby a thermal constant of said device for releasing heat to the flowing air is less than about 10 seconds.

2. The air temperature controlling device of claim 1, wherein said heating element comprises a gold coated electrically resistive material.

3. The air temperature controlling device of claim 1, wherein said heating element comprises a shape that enhances heat dissipation in moving air.

4. The air temperature controlling device of claim 1, wherein said heating element comprises a thin, electrically resistive ribbon.

5. The air temperature controlling device of claim 1, further comprising a shield substantially surrounding said heating element, said shield being open at opposite ends to allow air to pass therethrough.

6. The air temperature controlling device of claim 5, wherein at least one of said heating element and said shield is gold coated.

7. The air temperature controlling device of claim 5, further comprising at least one shield closing element mounted in one of said open opposite ends.

8. The air temperature controlling device of claim 7, wherein at least one of said heating element, said shield and said at least one shield closing element is gold coated.

9. The air temperature controlling device of claim 1, further comprising a passive element downstream of said heating element, wherein said passive element conditions a heat pulse generated when air flows over said heating element to transfer heat to the air during said air warming operation.

10. The air temperature controlling device of claim 1, further comprising a shield contained in said housing adjacent said heating element.

11. The air temperature controlling device of claim 1, further comprising a self-contained, portable power source adapted to connect with said heating element to supply said power thereto.

12. The air temperature controlling device of claim 1, wherein said power source comprises at least one electric cell.

13. The air temperature controlling device of claim 1, wherein said thermal time constant of said heating element in still air during said preheat operation is greater than about 20 seconds and said thermal time constant of said heating element in moving air during said warming operation is less than about 7 seconds.

14. The air temperature controlling device of claim 13, wherein said thermal time constant of said heating element in still air during said preheat operation is greater than about 30 seconds.

15. The air temperature controlling device of claim 14, wherein said thermal time constant of said heating element in still air during said preheat operation is greater than about 40 seconds and said thermal time constant of said heating element in moving air during said warming operation is less than about 5 seconds.

16. A hand-held, portable air temperature controlling device, comprising:

a heating element adapted to receive energy from a self-contained, portable power source and store said energy as heat during a preheat operation; and a housing surrounding said heating element and defining an air flow path through which air flows over said heating element to transfer heat to the air during an air warming operation;

wherein said heating element comprises a thin, electrically resistive ribbon and said device has a thermal time constant in still air during said preheat operation which is greater than about 10 seconds and a thermal time constant in moving air during said warming operation which is less than about 10 seconds.

17. The air temperature controlling device of claim 16, wherein said resistive ribbon is constructed of two banks and each said bank is configured into a series of narrow channels.

18. The air temperature controlling device of claim 16, wherein said resistive ribbon is configured into a series of narrow channels.

19. The air temperature controlling device of claim 18, further comprising a shield substantially surrounding said resistive ribbon, said shield having open opposite ends to allow air to pass therethrough.

20. The air temperature controlling device of claim 19, further comprising a shield closing element fitted in at least one of said open opposite ends.

21. The air temperature controlling device of claim 20, wherein each of said open opposite ends has a shield closing element fitted therein.

22. The air temperature controlling device of claim 20, wherein each said shield closing element comprises a mesh element.

23. A hand-held, portable air temperature controlling device, comprising:
- a heating element adapted to receive energy from a self-contained, portable power source and store said energy as heat during a preheat operation, said heating element comprising a thin, electrically resistive ribbon corrugated to form gaps to channel air therethrough;
- a shield substantially surrounding said resistive ribbon, said shield having open opposite ends to allow air to pass therethrough;
- a shield closing element fitted in each of said open opposite; and
- a housing surrounding said heating element and, together with said gaps in said ribbon, defining an air flow path through which air flows over said heating element to transfer heat to the air during an air warming operation.

24. The air temperature controlling device of claim 23 wherein said resistive ribbon comprises a plurality of banks and each said bank is configured into a series of narrow channels forming said gaps.

25. The air temperature controlling device of claim 24, wherein said resistive ribbon is constructed of two of said banks.

26. The air temperature controlling device of claim 23 wherein each said shield closing element comprises a mesh element.

27. The air temperature controlling device of claim 23 further comprising a passive element downstream of said resistive ribbon, wherein said passive element conditions a heat pulse generated when air flows over said heating element to transfer heat to the air during said air warming operation.

* * * * *

UNITED STATES PATENT AND TRADEMARK OFFICE
CERTIFICATE OF CORRECTION

PATENT NO. : 6,694,975 B2
DATED : February 24, 2004
INVENTOR(S) : Schuster, Jeffrey A. et al.

It is certified that error appears in the above-identified patent and that said Letters Patent is hereby corrected as shown below:

Column 27,
Line 44, delete claim 1 and insert the following:
    1. A hand-held, portable air temperature controlling device, comprising:
    a heating element adapted to receive energy from a self-contained, portable power source and store said energy as heat during a preheat operation; and
    a housing surrounding said heating element and defining an air flow path through which air flows over said heating element to transfer heat to the air during an air warming operation;
    wherein a thermal time constant of said device in still air during said preheat operation is greater than about 15 seconds and a thermal time constant of said device element in moving air during said air warming operation is less than about 15 seconds.

Signed and Sealed this

Twenty-second Day of June, 2004

JON W. DUDAS
*Acting Director of the United States Patent and Trademark Office*